US010548503B2

(12) United States Patent
Bosua

(10) Patent No.: US 10,548,503 B2
(45) Date of Patent: Feb. 4, 2020

(54) HEALTH RELATED DIAGNOSTICS EMPLOYING SPECTROSCOPY IN RADIO / MICROWAVE FREQUENCY BAND

(71) Applicant: Know Labs, Inc., Seattle, WA (US)

(72) Inventor: Phillip Bosua, Seattle, WA (US)

(73) Assignee: KNOW LABS, INC., Seattle, WA (US)

( * ) Notice: Subject to any disclaimer, the term of this patent is extended or adjusted under 35 U.S.C. 154(b) by 0 days.

(21) Appl. No.: 16/405,749

(22) Filed: May 7, 2019

(65) Prior Publication Data

US 2019/0357800 A1 Nov. 28, 2019

Related U.S. Application Data

(60) Provisional application No. 62/668,567, filed on May 8, 2018.

(51) Int. Cl.
| | |
|---|---|
| *A61B 5/05* | (2006.01) |
| *A61B 5/00* | (2006.01) |
| *A61B 5/145* | (2006.01) |
| *A61B 5/1455* | (2006.01) |
| *A61B 5/107* | (2006.01) |

(52) U.S. Cl.
CPC .......... *A61B 5/0507* (2013.01); *A61B 5/0075* (2013.01); *A61B 5/14532* (2013.01); *A61B 5/14552* (2013.01); *A61B 5/1071* (2013.01); *A61B 5/681* (2013.01); *A61B 5/6831* (2013.01)

(58) Field of Classification Search
CPC ........... A61B 5/14532; A61B 5/10507; A61B 5/0075; A61B 5/6831; A61B 5/681; A61B 5/1071

USPC .................. 600/365, 407, 410, 430
See application file for complete search history.

(56) References Cited

U.S. PATENT DOCUMENTS

| | | | | |
|---|---|---|---|---|
| 9,198,607 | B2* | 12/2015 | Fischer | A61B 5/0507 |
| 9,864,024 | B2* | 1/2018 | Vester | G01R 33/3628 |
| 10,149,629 | B2* | 12/2018 | Szczepaniak | A61B 5/053 |
| 2003/0036713 | A1* | 2/2003 | Bouton | A61B 5/05 |
| | | | | 600/587 |

(Continued)

FOREIGN PATENT DOCUMENTS

| | | |
|---|---|---|
| JP | 2012-125382 A | 7/2012 |
| KR | 10-2016-0081740 A | 7/2016 |
| WO | 2017/163245 A1 | 9/2017 |

OTHER PUBLICATIONS

International Search Report and Written Opinion for PCT/US2019/031176, dated Aug. 23, 2019, 9 pages.

(Continued)

*Primary Examiner* — Boniface N Nganga
(74) *Attorney, Agent, or Firm* — Cozen O'Connor

(57) ABSTRACT

An automated medical diagnostic system includes antennas, transmitter, receiver, and a processor-based device or system. Excitations signals are transmitted into bodily tissue at each of a plurality of discrete frequencies (e.g., steps of 1 MHz from 300 MHz to 2500 MHz) or unequal steps. The response signals are received and analyzed against the excitation signals at each of a number of the frequencies, for example determining gain/loss due to passage through bodily tissue. The results are analyzed for patterns indicative of a presence or absence of an abnormal condition, and results presented.

29 Claims, 16 Drawing Sheets

(56) References Cited

U.S. PATENT DOCUMENTS

| | | | |
|---|---|---|---|
| 2004/0065158 A1* | 4/2004 | Schrepfer | A61B 5/05 |
| | | | 73/864.81 |
| 2004/0127777 A1* | 7/2004 | Ruchti | A61B 5/0071 |
| | | | 600/316 |
| 2004/0133086 A1* | 7/2004 | Ciurczak | G16H 40/67 |
| | | | 600/322 |
| 2009/0275814 A1 | 11/2009 | Watanabe et al. | |
| 2010/0041969 A1 | 2/2010 | Beise | |
| 2014/0213870 A1 | 7/2014 | Hsu et al. | |
| 2017/0095667 A1 | 4/2017 | Yakovlev et al. | |
| 2018/0028824 A1 | 2/2018 | Pivonka et al. | |
| 2019/0008422 A1 | 1/2019 | Leath et al. | |

OTHER PUBLICATIONS

Qiang et al., "Quantitative detection of glucose level based on radiofrequency patch biosensor combined with volume-fixed structures," *Biosensors and Bioelectronics* 98:357-363, 2017.

\* cited by examiner

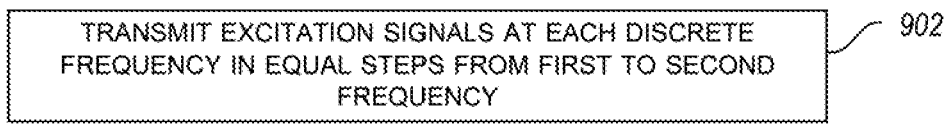

```
TRANSMIT EXCITATION SIGNALS AT EACH DISCRETE
FREQUENCY IN EQUAL STEPS FROM FIRST TO SECOND
FREQUENCY
```

FIG. 9

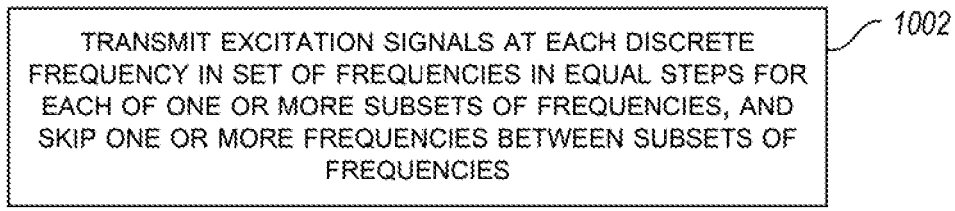

```
TRANSMIT EXCITATION SIGNALS AT EACH DISCRETE
FREQUENCY IN SET OF FREQUENCIES IN EQUAL STEPS FOR
EACH OF ONE OR MORE SUBSETS OF FREQUENCIES, AND
SKIP ONE OR MORE FREQUENCIES BETWEEN SUBSETS OF
FREQUENCIES
```

FIG. 10

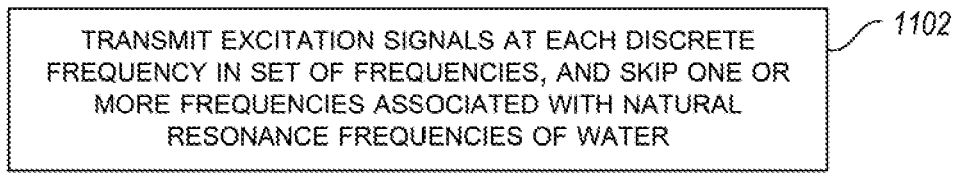

```
TRANSMIT EXCITATION SIGNALS AT EACH DISCRETE
FREQUENCY IN SET OF FREQUENCIES, AND SKIP ONE OR
MORE FREQUENCIES ASSOCIATED WITH NATURAL
RESONANCE FREQUENCIES OF WATER
```

FIG. 11

HEALTH RELATED DIAGNOSTICS EMPLOYING SPECTROSCOPY IN RADIO / MICROWAVE FREQUENCY BAND

BACKGROUND

Technical Field

The present disclosure generally relates to a medical diagnostics, and, more particularly, to apparatus, systems and methods to perform diagnostics via spectroscopic techniques applied to non-optical frequencies such as the radio and, or microwave frequency bands of the electromagnetic spectrum.

Description of the Related Art

It is important to assess health and otherwise perform medical diagnostics on humans and other animals. There are numerous instruments and techniques for assessing health and, or performing medical diagnostics. Many of these techniques are invasive, for example blood draws. Many of these techniques require time, for example lab testing. Many of these techniques are intrusive, for example use of a blood pressure cuff. Many of these techniques are performed only on demand, for instance at a yearly physical examination or when presenting at an emergency room or urgent care facility.

BRIEF SUMMARY

Health care assessment or medical diagnostics would preferably be performed in a non-invasive manner. Health care assessment or medical diagnostics would preferably be performed in an non-obtrusive manner. Health care assessment or medical diagnostics would preferably be performed on a consistent basis, for example daily, hourly or even continuously or near continuously, and in real or almost real time.

Health care assessment or medical diagnostics can be performed via an apparatus or article which is non-invasive, non-intrusive, and, or which monitors health on a periodic basis one or more times a day, and even on an hourly, or minute-by-minute basis, or even continuously or near-continuously, and which can provide real time or almost real time results. In at least some implementations, an interface is worn by a subject in an unobtrusive manner, for example as a band worn around a portion of an appendage. The interface includes one or more antennas to transmit excitations signals through adjacently located bodily tissue, and to receive response signals and compare these response signals to the excitation signals after they pass through the bodily tissue. The excitation signals and the response signals are preferably in non-optical (i.e., outside the visible, infrared, ultraviolet bands) portions or bands of the electromagnetic spectrum, for instance the radio and, or microwave frequency bands of the electromagnetic spectrum.

The excitations signals are generated via one or more transmitters, operable to generate and provide excitation signals at each of a plurality of discrete frequencies over a set or a plurality of frequencies, for instance from 300 MHz to 2500 MHz. The response signals are received via one or more receivers that is operable to receive signals at each of a plurality of discrete frequencies over a set of a plurality of frequencies, for instance from 300 MHz to 2500 MHz.

An automated medical diagnostic system, for example a processor-based system, is operable to determine differences between the response signals and the respective excitation signals that gave rise to the respective response signals. Thus, the processor-based system is operable to assess signals such as S parameters and/or transition line parameters and/or dielectric parameters. An example being the amount of gain or loss (e.g., dB) between the excitation signals and the corresponding response signals which results from passage of the signals through at least a portion of bodily tissue that is being assessed or sampled. At least some of these determined differences are the result of, and hence characterize, one or more physical conditions or states of the bodily tissue or concentrations of material within the bodily tissue at the time of the assessment or performance of the medical diagnostics, referred to herein as sampling.

The automated medical diagnostic system can compare the determined differences to a set of baseline determined differences, collected at a previous time, and which characterize one or more physical conditions or states of the bodily tissue at a baseline state, for example producing a set of differences between the current state values and the baseline state values. The baseline state may represent a healthy state, or may simply represent a starting state, whether the subject is considered healthy at that time or not. The baseline state may represent a baseline for the particular subject being assessed, or may represent a generic baseline common across many subjects. The automated medical diagnostic system may compare a difference between one or more of the sampling state values (e.g., differences between the excitation and response signals captured at a current or sampling time) and one or more of the baseline state values (e.g., differences between the excitation and response signals captured at a baseline time). The automated medical diagnostic system may assess whether a defined pattern exists or is absent from the differences, and provide an indication of a presence or absence of an anomalous physical condition or other difference or null difference of the subject based on the comparison identified.

Commercial implementation of such an automated medical diagnostic system may require that the overall cost is competitive, the results are highly accurate, and the automated medical diagnostic easy to use in a non-invasive and non-obtrusive manner. Consequently, a new approach to health assessment and diagnostics of bodily tissue is highly desirable.

A device that interfaces with bodily tissue to perform in vivo diagnostics may be summarized as including a first antenna; at least a second antenna, the second antenna spaced laterally with respect to the first antenna by a first range of distances that provide for near field communications between the first and the second antennas; and at least one electromagnetic force (EMF) shield positioned with respect to the first and the second antennas that provides a communicative path between the first and the second antennas in a first direction through a mounting interface that in use is proximally adjacent the bodily tissue and that mostly electromagnetically isolates the second antenna from direct communications with the first antenna except along a path that passes through the bodily tissue. The at least one EMF shield electromagnetically may be a sheet of a metal foil or a conductive paint and/or coating.

The device may further include a first plastic body to which the first antenna is attached; and a second plastic body to which the second antenna is attached. The first plastic body may selectively mate to the second plastic body to laterally space the second antenna with respect to the first antenna. The first plastic body may have a slot to receive a portion of the sheet of metal foil and position the sheet of metal foil to prevent direct communications between the first and the second antennas. The at least one EMF shield electromagnetically may be a sheet of a printed circuit board with a metal layer. The at least one EMF shield electromagnetically may isolate the first antenna from a surrounding environment except in a first direction which faces the bodily tissue in use. The at least one EMF shield electromagnetically may isolate the second antenna from a surrounding environment except in a first direction. The at least one EMF shield electromagnetically may isolate the first antenna from a surrounding environment except in the first direction. The bodily tissue may be the epidermis and the first direction may face the epidermis and may be spaced therefrom by a second range of distances in use. The second antenna may be spaced laterally from the first antenna by a distance in a range of 0.1 mm to 50 mm, inclusive and/or varying the distance based on the frequency being used or for any other reason.

A system to perform in vivo diagnostics on bodily tissue may be summarized as including a transmitter coupled or coupleable to at least one antenna and operable to transmit a plurality of excitation signals at each of a plurality of wavelengths in at least one of a radio frequency band and, or, a microwave frequency band of the electromagnetic spectrum via at least one antenna; a receiver coupled or coupleable to at least one antenna and operable to receive a plurality of response signals to the excitation signals which are returned through or from the bodily tissue via at least one antenna in response to the excitation signals and which represent at least one physical characteristic of the bodily tissue from which the response signals are returned; at least one processor; and at least one nontransitory processor-readable medium that stores at least one of processor-executable instructions or data which, when executed by the at least one processor, cause the at least one processor to: for a first sampling cycle, for each of a number of the plurality of wavelengths, determine a sampling difference between a respective excitation signal and a respective response signal at the respective wavelength; for each of a number of the plurality of wavelengths, determine a sampling to baseline difference between the determined sampling difference and a respective baseline difference for the respective wavelength, the baseline difference which represents a difference between a baseline excitation signal at the respective wavelength and a baseline response signal at the respective wavelength, each baseline response signal which represent respective response to the respective baseline excitation signal at the respective frequency for a baseline physical condition of the bodily tissue; compare at least some of the determined sampling to baseline differences to defined pattern of differences; and indicate an existence or absence of an anomalous physical condition based on the comparison of at least some of the determined sampling to baseline differences to a defined pattern of differences.

The system may further include for a second sampling cycle, for each of a number of the plurality of wavelengths, determine a sampling difference between a respective excitation signal and a respective response signal at the respective wavelength; for each of a number of the plurality of wavelengths, determine a sampling to baseline difference between the determined sampling difference and a respective baseline difference for the respective wavelength, the baseline difference which represents a difference between a baseline excitation signal at the respective wavelength and a baseline response signal at the respective wavelength, each baseline response signal which represent respective response to the respective baseline excitation signal at the respective frequency for a baseline physical condition of the bodily tissue. The at least one of processor-executable instructions or data, when executed by the at least one processor, may cause the at least one processor to: compare at least some of the determined sampling to baseline differences to defined pattern of differences for the sampling response signals collected during both the first and the second sampling cycles.

The system may further include for a third sampling cycle, for each of a number of the plurality of wavelengths, determine a sampling difference between a respective excitation signal and a respective response signal at the respective wavelength; for each of a number of the plurality of wavelengths, determine a sampling to baseline difference between the determined sampling difference and a respective baseline difference for the respective wavelength, the baseline difference which represents a difference between a baseline excitation signal at the respective wavelength and a baseline response signal at the respective wavelength, each baseline response signal which represent respective response to the respective baseline excitation signal at the respective frequency for a baseline physical condition of the bodily tissue. The at least one of processor-executable instructions or data, when executed by the at least one processor, may cause the at least one processor to: compare at least some of the determined sampling to baseline differences to defined pattern of differences for the sampling response signals collected during the first, the second, and the third sampling cycles. The at least one of processor-executable instructions or data, when executed by the at least one processor, may cause the at least one processor to: for each of the frequencies, average two or more response signals to the respective excitation signal at the respective frequency which are returned through or from the bodily tissue over a period of time. The at least one of processor-executable instructions or data, when executed by the at least one processor, may cause the at least one processor to: for each of the frequencies, sequentially transmit two or more excitation signals at the respective frequency over a period of time. The at least one of processor-executable instructions or data, when executed by the at least one processor, may cause the at least one processor to: ignore at least one response signal to the respective excitation signal for at least one of the frequencies.

The transmitter may transmit the plurality of excitation signals at each of the plurality of discrete frequencies in equal steps or unequal steps from a first frequency to a second frequency. The transmitter may transmit the plurality of excitation signals at each of the plurality of discrete frequencies in equal steps (e.g., 1 MHz or 10 MHz) or unequal steps, from a first frequency to a second frequency. The transmitter may transmit the plurality of excitation signals at each of the plurality of discrete frequencies in equal steps or unequal steps from a first frequency of approximately 300 MHz to a second frequency. The transmitter may transmit the plurality of excitation signals at each of the plurality of discrete frequencies in equal steps or unequal steps from a first frequency to a second frequency of approximately 2500 MHz. The transmitter may transmit the plurality of excitation signals at each of the plurality of discrete frequencies in equal steps or unequal steps from 300 MHz to 2500 MHz. The transmitter may transmit the plurality of excitation signals at each of the plurality of discrete frequencies in a set of frequencies in equal steps or unequal steps for each of one or more subsets of frequencies in the set of frequencies, and may skip one or more frequencies between the subsets of frequencies. The transmitter may transmit the plurality of excitation signals at each of the plurality of discrete frequencies in a set of frequencies, and may skip one or more frequencies associated with one or more natural resonance frequencies of interfering substances, for example water.

The system may further include an interface that interfaces with the bodily tissue, the interface comprising: a first antenna; at least a second antenna, the second antenna spaced laterally with respect to the first antenna by a first range of distances; and at least one electromagnetic force (EMF) shield which electromagnetically isolates the second antenna from the first antenna except via a path that passes through the bodily tissue when the interface is positioned with respect to the bodily tissue. The first antenna may be communicatively coupleable to the transmitter and the second antenna is communicatively coupleable to the receiver. The at least one EMF shield electromagnetically may be a sheet of a metal foil or conductive paint and/or coating. The at least one EMF shield electromagnetically may isolate the second antenna from a surrounding environment except in a first direction. The at least one EMF shield electromagnetically may isolate the first antenna from a surrounding environment except in the first direction. The first antenna may have a main lobe of emission, and the main load of emission of the first antenna may extend principally along the first direction. The bodily tissue may be the epidermis and the first direction may face the epidermis and may be spaced therefrom by a second range of distances in use. All communications between the transmitter and the receiver may be via near field communications without far field communications therebetween (not to be confused with far field communication to send the collected data to a cloud/phone/computer). The at least one of the processor-executable instructions or data may cause the processor to determine whether at least some of the determined sampling to baseline differences are within a range defined by a lower threshold value and an upper threshold value.

A method of performing in vivo diagnostics on bodily tissue may be summarized as including operating a transmitter coupled or coupleable to at least one antenna to transmit a plurality of excitation signals at each of a plurality of wavelengths in at least one of a radio frequency band and, or, a microwave frequency band of the electromagnetic spectrum via at least one antenna; receiving via a receiver coupled or coupleable to at least one antenna a plurality of response signals to the excitation signals which are returned from the bodily tissue via at least one antenna in response to the excitation signals and which represent at least one physical characteristic of the bodily tissue from which the response signals are returned; for a first sampling cycle, for each of a number of the plurality of wavelengths, determining, via at least one processor, a sampling difference between a respective excitation signal and a respective response signal at the respective wavelength; for each of a number of the plurality of wavelengths, determining, via at least one processor, a sampling to baseline difference between the determined sampling difference and a respective baseline difference for the respective wavelength, the baseline difference which represents a difference between a baseline excitation signal at the respective wavelength and a baseline response signal at the respective wavelength, each baseline response signal which represent respective response to the respective baseline excitation signal at the respective frequency for a baseline physical condition of the bodily tissue; comparing, via at least one processor, at least some of the determined sampling to baseline differences to defined pattern of differences; and causing, via at least one processor, an indicate an existence or absence of an anomalous physical condition to be provided based on the comparison of at least some of the determined sampling to baseline differences to defined pattern of differences.

The method may further include for a second sampling cycle, for each of a number of the plurality of wavelengths, determining, via the at least one processor, a sampling difference between a respective excitation signal and a respective response signal at the respective wavelength; and for each of a number of the plurality of wavelengths, determining, via the at least one processor, a sampling to baseline difference between the determined sampling difference and a respective baseline difference for the respective wavelength, the baseline difference which represents a difference between a baseline excitation signal at the respective wavelength and a baseline response signal at the respective wavelength, each baseline response signal which represent respective response to the respective baseline excitation signal at the respective frequency for a baseline physical condition of the bodily tissue. The comparing at least some of the determined sampling to baseline differences to defined pattern of differences may include comparing at least some of the determined sampling to baseline differences to defined pattern of differences for the sampling response signals collected during both the first and the second sampling cycles.

The method may further include for a third sampling cycle, for each of a number of the plurality of wavelengths, determining, via the least one processor a sampling difference between a respective excitation signal and a respective response signal at the respective wavelength; and for each of a number of the plurality of wavelengths, determining, via the at least one processor, a sampling to baseline difference between the determined sampling difference and a respective baseline difference for the respective wavelength, the baseline difference which represents a difference between a baseline excitation signal at the respective wavelength and a baseline response signal at the respective wavelength, each baseline response signal which represent respective response to the respective baseline excitation signal at the respective frequency for a baseline physical condition of the bodily tissue. Comparing at least some of the determined sampling to baseline differences to defined pattern of differences may include comparing at least some of the determined sampling to baseline differences to a defined pattern of differences for the sampling response signals collected during the first, the second, and the third sampling cycles.

The method may further include for each of the frequencies, averaging two or more response signals to the respective excitation signal at the respective frequency which are returned from the bodily tissue over a period of time. Operating a transmitter to transmit a plurality of excitation signals at each of a plurality of wavelengths may include operating the transmitter to, for each of the frequencies, sequentially transmitting two or more excitation signals at the respective frequency over a period of time.

The method may further include ignoring at least one response signal to the respective excitation signal for at least one of the frequencies. Operating a transmitter to transmit a plurality of excitation signals at each of a plurality of wavelengths may include operating the transmitter to transmit the plurality of excitation signals at each of the plurality of discrete frequencies in equal steps or unequal steps from a first frequency to a second frequency. Operating a transmitter to transmit a plurality of excitation signals at each of a plurality of wavelengths may include operating the transmitter to transmit the plurality of excitation signals at each of the plurality of discrete frequencies in equal steps (e.g., 1 MHz or 10 MHz) or unequal steps from a first frequency to a second frequency. Operating a transmitter to transmit a plurality of excitation signals at each of a plurality of wavelengths may include operating the transmitter to transmit the plurality of excitation signals at each of the plurality of discrete frequencies in equal steps or unequal steps from a first frequency of approximately 300 MHz to a second frequency. Operating a transmitter to transmit a plurality of excitation signals at each of a plurality of wavelengths may include operating the transmitter to transmit the plurality of excitation signals at each of the plurality of discrete frequencies in equal steps or unequal steps from a first frequency to a second frequency of approximately 2500 MHz. Operating a transmitter to transmit a plurality of excitation signals at each of a plurality of wavelengths may include operating the transmitter to transmit the plurality of excitation signals at each of the plurality of discrete frequencies in equal steps or unequal steps or unequal steps or unequal steps from 300 MHz to 2500 MHz.

Operating a transmitter to transmit a plurality of excitation signals at each of a plurality of wavelengths may include operating the transmitter to transmit the plurality of excitation signals at each of the plurality of discrete frequencies in a set of frequencies in equal steps or unequal steps for each of one or more subsets of frequencies in the set of frequencies, and skip one or more frequencies the subsets of frequencies.

Operating a transmitter to transmit a plurality of excitation signals at each of a plurality of wavelengths may include operating the transmitter to transmit the plurality of excitation signals at each of the plurality of discrete frequencies in a set of frequencies, and skips one or more frequencies associated with one or more natural resonance frequencies of water. All communications between the transmitter and the receiver may be via near field communications without far field communications therebetween.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 9 is low level a flow diagram showing a method of operation of an automated medical diagnostic system, according to at least one implementation, the method useful in performing the method of FIG. 6.

FIG. 10 is low level a flow diagram showing a method of operation of an automated medical diagnostic system, according to at least one implementation, the method useful in performing the method of FIG. 6.

FIG. 11 is low level a flow diagram showing a method of operation of an automated medical diagnostic system, according to at least one implementation, the method useful in performing the method of FIG. 6.

DETAILED DESCRIPTION

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers and/or medical equipment have not been shown or described in detail to avoid unnecessarily obscuring descriptions of the embodiments.

Unless the context requires otherwise, throughout the specification and claims which follow, the word "comprise" and variations thereof, such as "comprises" and "comprising," are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Figure 1:
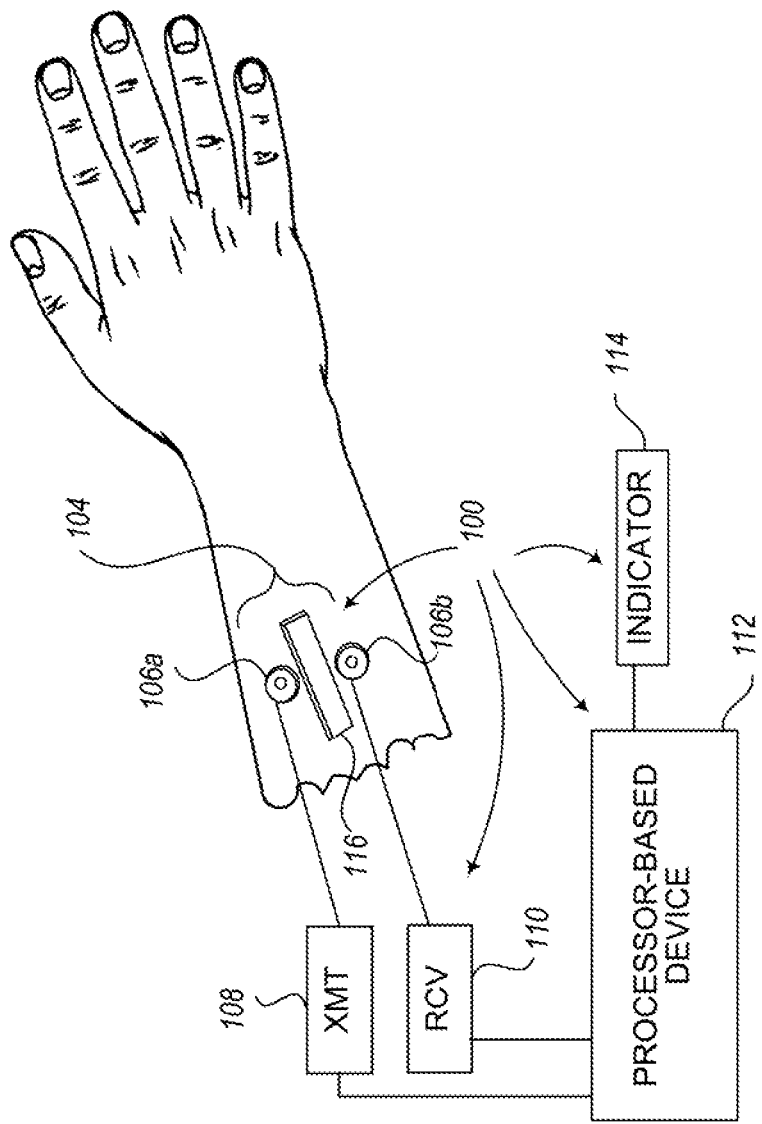
FIG. 1 is an isometric view of an automated medical diagnostic system to perform in vivo diagnostics on bodily tissue including a set of antenna, an optional EMF shield positioned or positionable between the antennas, a transmitter coupled to one of the antenna, a receiver coupled to an antenna, and a processor-based device coupled to at least the receiver, according to one illustrated implementation, the antennas positioned with respect to bodily tissue, illustrated as a forearm, wrist and hand.

FIG. 1 shows an automated medical diagnostic system 100 to perform health assessments or diagnostics on bodily tissue positioned relative to an example of bodily tissue 102, according to one illustrated implementation.

The automated medical diagnostic system 100 may include an interface 104 that comprises one or more antennas 106a, 106b (two shown, collectively 106) to couple excitation signals to bodily tissue 102 and to receive response signals therefrom. The automated medical diagnostic system 100 may include one or more transmitters 108 and one or more receivers 110 which are communicatively coupled to drive the antennas 106 to emit the excitation signals and to detect or receive the response signals. The automated medical diagnostic system 100 may include one or more processor-based devices or systems 112, communicatively coupled to the receiver 110 and optionally communicatively coupled to the transmitter 108, and operable to analyze the response signals returned from the body. The processor-based device or system 112 may include, or be communicatively coupled to an indicator 114, for example a visual indication (e.g., light emitting diode(s), liquid crystal display (LCD), or other visual display device), or to an aural or haptic indication (e.g., speaker, buzzer).

The automated medical diagnostic system 100, or components thereof (e.g., interface 104) may take any of a variety of forms, for example a system or device used in a clinical setting, although preferably one or more components take the form of a wearable device that can be unobtrusively worn by an individual for instance during normal, everyday routines. For example, in some implementations the interface 104 with the antennas 106, transmitter 108, receiver 110, and processor-based device or system 112 are all packaged together as a single integral wearable device (e.g., smartwatch, band, cuff or fitness tracker). In other implementations, the interface 104 with the antennas 106, transmitter 108, and receiver 110, are all packaged together as a single integral wearable device (e.g., smartwatch, band, cuff or fitness tracker), and the processor-based device or system 112 is separate or distinct from the single integral wearable device. The separate or distinct processor-based device or system 112 may, for example, take the form of a smartphone, a tablet computer that is proximate the interface, transmitter and receiver in use, for example within range of a Bluetooth radio and antenna. The separate or distinct processor-based device or system 112 may, for example, take the form of remotely located computer system (e.g., server computer, back end computer system) that is remote from the single integral wearable device, for example at a fixed location, and communicatively coupled via one or more network infrastructures. In such implementations, the single integral wearable device can communicate with the separate or distinct processor-based device or system 112 via any variety of wired and/or wireless communications infrastructures, for instance radios (e.g., WI-FI radios, cellular radios), base stations, the Internet, etc. Other forms of wireless, optical (e.g., infrared) or even wired communications may be employed.

The interface 104 may be as simple as two antennas 106, or may include a housing or other structure that spaces one of the antennas 106b laterally from the other one of the antennas 106a, as discussed and illustrated herein. The lateral spacing may, for example be 1 mm inclusive to 2 mm inclusive, although the antennas 106a, 106b may be spaced further apart (e.g., 1 mm to 20 mm), but within a distance in which near field communications occur between the antennas 106a, 106b via the bodily tissue 102. The interface 104 may be shaped and sized to position the antennas 106a, 106b adjacent or proximate to the bodily tissue 102, for example close to, but not in contact with the bodily tissue 102. While illustrated as a forearm, wrist and hand, the bodily tissue 102 can take the form of any other portion of bodily tissue, for example the earlobe or abdomen.

As discussed in detail below, the interface 104 may include the antennas 106 and an optional shield (e.g., EMF shield) 116 that prevents or substantially (e.g., equal to or greater than 30 dB reduction) limits wireless communications (e.g., communications in the radio frequency band and/or microwave frequency band) directly between the antennas 106a, 106b, causing near field wireless communications between the antennas 106a, 106b to pass at least partially through the bodily tissue 102. As described herein, the shield 116 can take a variety of forms, for example an electrically conductive material, for instance a metal. The shield 116 may, for example, include stainless steel, or more preferably a metal foil (e.g. aluminum foil, copper foil), or a metalized flexible substrate, for instance a metalized Mylar®, metalized paper polyethylene, metalized plastic laminate, cardboard, fiberboard, conductively filled paint or coating, etc. The metal acts as a shield (e.g., partial Faraday cage). The shield 116 may, for example, include a metal sheet or foil, a wire metal mesh, metal coated film, or printed circuit board with a metal layer. A large variety of metals may be suitable, e.g., copper, aluminum. A large variety of thicknesses may be suitable. The shield 116 should have sufficient dimensions (e.g., length, width, thickness, diameter, circumference) to ensure that the response signals are received via at least one of the antennas (e.g., receiving antenna) 106.

Various structures are referred to as shielded, that is shielded at least from certain radio frequencies or wavelengths and/or microwave frequencies or wavelengths in the frequency ranges or wavelength ranges at which the automated medical diagnostic system operate, i.e., frequency ranges or wavelength ranges of excitation signals transmitted by the transmitters and/or frequency ranges or wavelength ranges of response signals received by the receivers. The shield may be a Faraday cage or partial Faraday cage, that sufficiently attenuates electromagnetic signals as to prevent communications directly between the antennas 106 without passing at least partially through the bodily tissue. The shield can comprise sheets and/or meshes of conductive material (e.g., aluminum, copper, silver, gold, mild steel), of sufficient conductivity, thickness, and geometry as to cause attenuation (e.g., 30 dB, 50 dB; 60 dB reduction via a silver coated nylon fabric; 85 dB reduction via aluminum foil, 120 dB reduction via Mu-copper foil of 0.12 mm thick) in the particular wavelength or frequency ranges of interest (e.g., 350 MHz-2500 MHz). Where a mesh is employed, the holes or apertures of the mesh should have a characteristic dimension that is much smaller (e.g., ¼ wavelength) than the wavelength of the signal to be stopped (i.e., excitation signal and/or response signal).

The antennas 106 can take a variety of forms, the shapes and sizes suitable to the particular frequency ranges which will be employed. For example, the antennas 106 may take the form of coil antennas, dipole antennas, and/or slot antennas. Portions of one or more of the antennas 106 may overlap. For example, where the antennas 106 are coil antennas, each formed of one or more coils, a portion of an area enclosed by an outermost coil of each antenna may overlap a portion of an area enclosed by an outermost coil of a neighboring antenna. In such implementations, neighboring antennas 106 may be electrically insulated from one another, for example by one or more electrically insulative layers or substrates. For example, successively adjacent antennas 106 may be carried on opposite surfaces (e.g., opposed outer surfaces, or multiple inner surfaces, or one or more outer and inner surfaces) of a single substrate. A simple antenna with a circular profile may be suitable for a range of 350 MHz inclusive to 2500 MHz inclusive. While illustrated as being substantially the same shape and size as each other, the antennas 106a, 106b may have different shapes and sizes from one another. The antennas 106 may each have a principal axis or node of transmission/reception. The antennas 106 are positioned to orient the principal axis or node of transmission/reception in a shared direction (e.g., generally parallel to one another plus or minus 15°). The principle axis can, for example, be any angle except directly 90°—in some instances it will be more desirable to have the principal axes at an angle between 0° and 89° depending on the position on the body and the design of the antenna. (Note: 0°-89°/91°-179°/181°-269°/271°-359° are the same thing, which is a direction in which the interface 104 will face the bodily tissue 102 when in use or positioned for use.) The antennas may lie in the same plane, or in respective planes that are parallel to one another. Alternatively, antennas may lie on non-planar surfaces, for instance conical surfaces (e.g., concave, convex). Thus, the antennas may be positioned on a same side of surface of bodily tissue as one another, allowing one antenna to receive a return (e.g., reflectance, transflectance) of a signal transmitted by the other antenna after partially traversing the bodily tissue, for example after penetrating a sufficient distance to reach blood flow through vessels or capillaries.

The transmitter 108 and associated antenna(s) 106a are operable to cause excitation signals to be emitted at each of a plurality of discrete frequencies in a range, in a direction at least partially along the principal axis or node of transmission/reception. The transmitter 108 may, for example, step through a range of frequencies, for instance in equal steps (e.g., 10 MHz steps) or unequal steps. The transmitter 108 may, for example, skip some frequencies or subsets of frequencies, for instance as described elsewhere herein. The receiver 110 and associated antenna(s) 106b are operable to receive response signals at each of a plurality of discrete frequencies in a range. The received response may return along the principal axis or node of transmission/reception of the antenna 106b. The excitation signals and the response signals may, for example, be in a non-optical portion of the electromagnetic spectrum, and may for instance be from the radio frequency and/or microwave frequency portions of the electromagnetic spectrum. The excitation signals and the response signals may, for example, be within the range or set of frequencies extending from approximately 350 MHz inclusive through 2500 MHz inclusive, or may be comprise one or more portions or subsets of that range, which may or may not be contiguous portions or subsets of that range or may or may not be non-contiguous portions or subsets of that range.

While described in more detail below with reference to FIG. 5, the processor-based device or system 112 processes the response signals, the response signals which represent one or more physical characteristics (e.g., glucose levels, blood pressure, pulse, oxygen level and/or blood gases) of the bodily tissue, and hence of the body or health of a subject being tested or sampled. In particular, during operation or "sampling" the processor-based device or system 112 determines differences between response signals and excitation signals at each of a plurality of frequencies. The processor-based device or system 112 compares the determined differences from the sampling to a set of determined differences that represent a baseline. The baseline represents one or more physical characteristics of the bodily tissue at a baseline condition. The baseline condition can, for example, be a healthy subject or subject perceived as being healthy. The baseline condition can, for example, be specific to the subject currently undergoing sample, the baseline having been measured or established at a previous time (i.e., prior to the current sampling or testing of the same subject). The baseline condition can, for example, be generic, the baseline having been measured or established at a previous time (i.e., prior to the current sampling or testing) across a plurality of different subjects, who may or may not have some physical trait in common, for instance gender, age, ethnicity. Based on the comparison, the processor-based device or system 112 determines whether there is one or more patterns, for instance peaks in the differences at certain frequencies or groups of peaks in the differences at certain frequencies, the pattern representative of the presence or absence of an abnormality (e.g., one or more of a combination of disease conditions, elevated blood sugar level in a diabetic subject). In evaluating the patterns, the processor-based device or system 112 may focus on certain values or differences in values at only selected frequencies, while ignoring values or differences in values at other frequencies. In evaluating the patterns, the processor-based device or system 112 may ignore unusually large values or large differences in values, even those corresponding to peaks in differences, or ignore unusually small values or small differences in values, for example using only values or differences in values that are within a desired range of values or desired range of differences in values.

Figure 2:
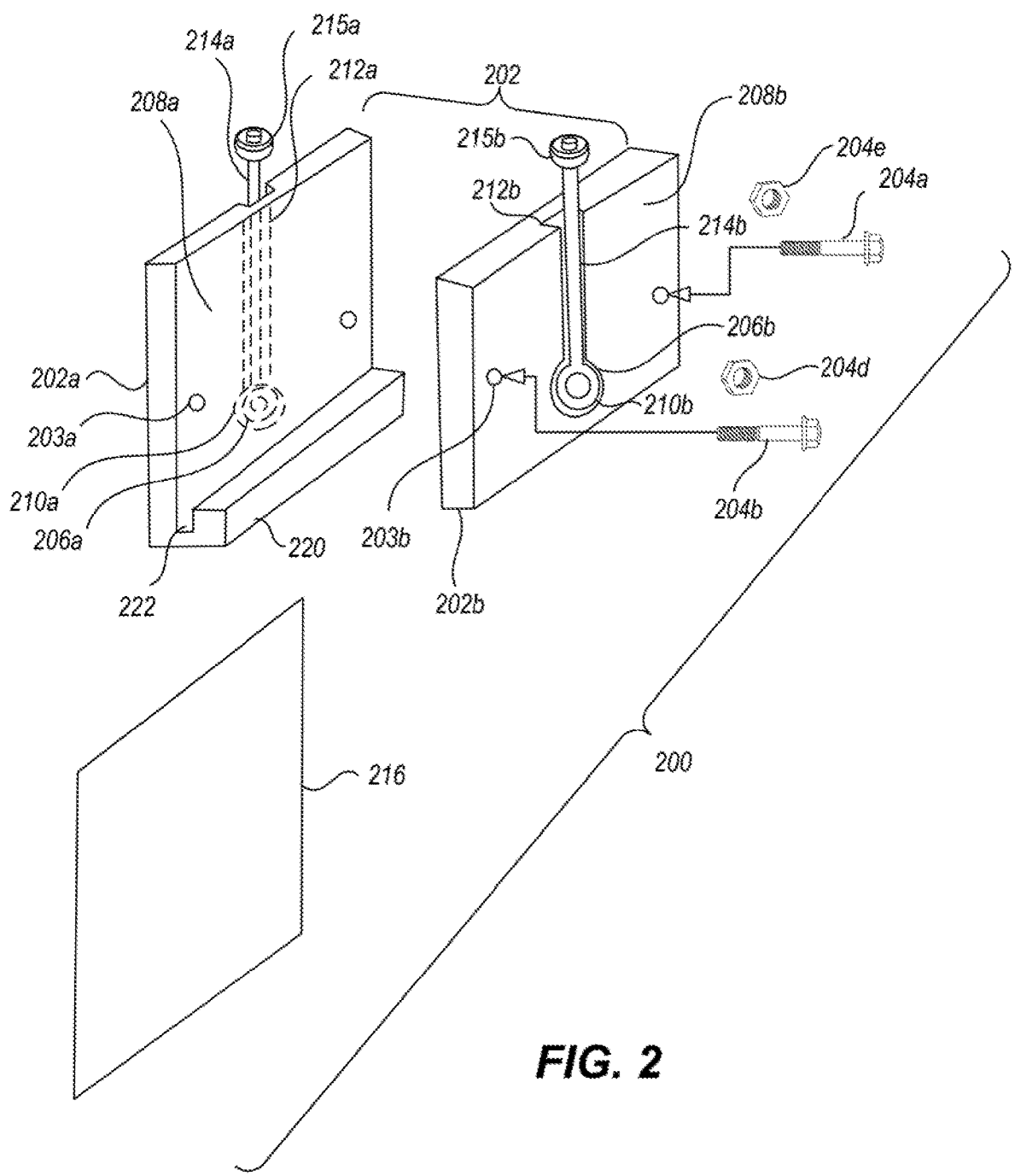
FIG. 2 is an exploded view of an interface of an automated medical diagnostic system, the interface comprising a housing, a set of antennas, an optional EMF shield positioned or positionable between the antennas in the housing, and a number of fasteners fasten portions of the housing together, according to at least one illustrated implementation.

FIG. 2 shows an interface 200 of an automated medical diagnostic system, according to one illustrated implementation. The interface 200 can be used with the processor-based device or system 112 of FIG. 1, or with other processor-based devices or systems.

The interface 200 includes a housing or spacing structure 202, which may be comprised of two portions 202a, 202b. The two portions 202a, 202b may be selectively mateable to one another. For example, the two portions 202a, 202b may have throughholes 203a, 203b (only two called out), via which one or more fasteners (e.g., bolts 204a, 204b) are received and secured, for instance via threads and, or nuts 204c, 204d. The fasteners are collectively referred to as 204. Respective pairs of the throughholes 203a, 203b preferably align when the two portions 202a, 202b are put together or mated.

Each portion 202a, 202b holds a respective antenna 206a, 206b. The portions 202 may each have a major face 208a, 208b with a respective recess 210a, 210b in which the respective antennas 206a, 206b is received. A depth of the recess 210a, 201b may be sufficient such that the antennas 206a, 206b are below a respective face (e.g., outward faces) 208a, 208b of the portions 202a, 202b of the housing 202. A thickness of a part of each portion 202a, 202b may laterally separate a first one of the antenna 106a from a second one of the antenna 106b, for example by a defined distance. Each portion 202a, 202b may include a channel 212a, 212b to provide a path for a respective lead 214a, 214b to/from the antennas 206a, 206b. A portion of each of the leads 214a, 214b may be recessed in the major face 208a, 208b of the respective portions 202a, 202b of the housing 202. The leads 214a, 214b may have connectors or couplers, for example coaxial connectors 215a, 215b, used to make physical and communicative connections or couplings, for instance to a transmitter and receiver (not illustrated in FIG. 2).

The interface 200 advantageously includes a space between the portions 202a, 202b to receive a shield (e.g., EMF shield) 216. The shield 216 can be similar or even identical to the shield 116 described in reference to FIG. 1.

A first one of the portions 202a includes a leg or shelf 220, the portion having an generally L-shaped cross-section. A second one of the portions 202b may sit on the leg or shelf 220 when the portions 202a, 202b are mated. The first one of the portions 202a includes a channel or slot 222, sized to accommodate an edge of the shield 216, and to position the shield 216 to be relatively proud of the antennas 206a, 206b when the interface 200 is assembled. Such may eliminate or substantially reduce direct communications between the antennas 206a, 206b, so that response signals received are those that pass at least partially through the bodily tissue. The shield is preferably positioned to prevent or significantly inhibit transmission and, or reception of the antennas along directions other than along the principal axis or node of transmission/reception, and should extend outwardly of the antenna to prevent or inhibit communications in other directions.

Figure 3:
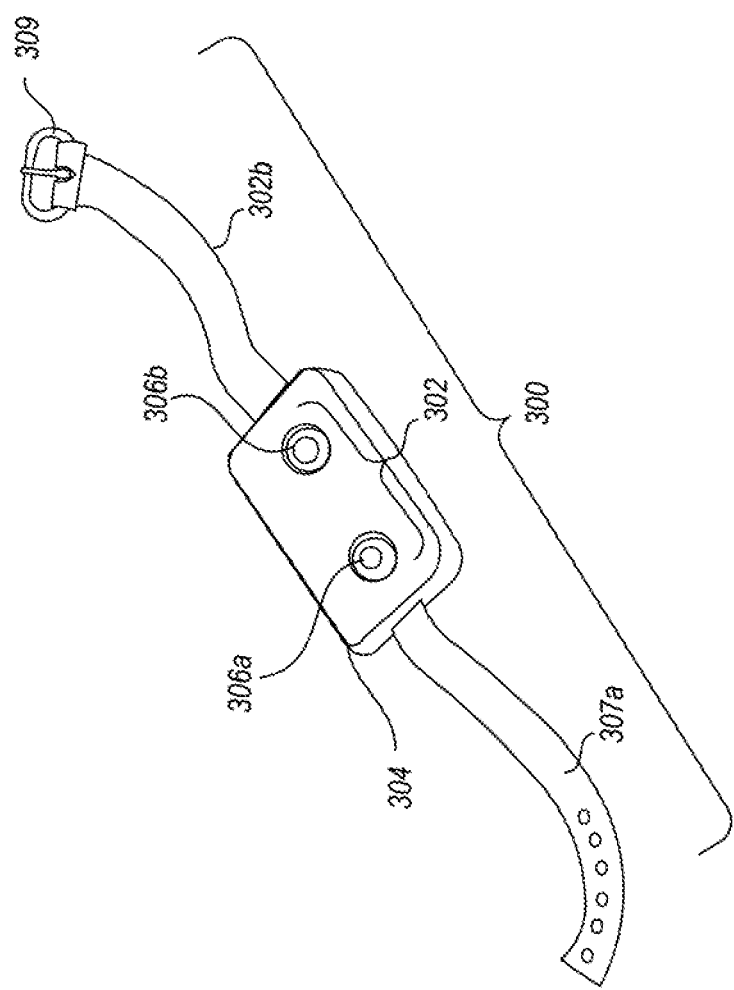
FIG. 3 is an isometric view of a wearable device such as a smartwatch or fitness tracker that forms all or a portion of an automated medical diagnostic system and which includes a housing, a set of antennas, an optional EMF shield positioned or positionable between the antennas in the housing, according to at least one illustrated implementation.

FIG. 3 shows a wearable device 300 that forms all or a portion of an automated medical diagnostic system and that may be worn on a portion of bodily tissue of a subject, or example worn on a limb, according to one illustrated implementation.

The wearable device 300 includes an interface 302 including a pair of antennas 306a, 306b positioned to provide near field communications therebetween via the bodily tissue. A portion of the wearable device 300, for example a housing 304, may serve as a shield or contain one or more shields which substantially electromagnetically isolates a second one of the antenna 306b from direct communications with a first one of the first antenna 306b except along a path (e.g., along the principal axis or node of transmission/reception) that passes through the bodily tissue. The housing 304 or shield(s) may, for example, substantially surround each of the antennas 306a, 306b except for a portion of the antennas 306a, 306b that faces the bodily tissue of the subject when the wearable device 300 is worn by the subject. As noted, the portion that faces the bodily tissue should be the portion along which the principal axis or node of transmission/reception extends. Thus, the housing 304 or shield(s) form a partial Faraday cage about each of the antennas 306a, 306b with each with one respective window to allow excitation signals to be transmitted to the bodily tissue over a defined near field communications path, and response signals to be received from the bodily tissue over a defined near field communications path.

The wearable device 300 includes may include a strap, for example with two strap portions 307a, 307b (collectively 307) which extend from the housing and which include a closure 309 operable to selectively securable attach the strap portions 307a, 307b together to attach the wearable device 300 to a limb or appendage of a subject.

The wearable device 300 includes a transmitter and receiver (not visible in FIG. 3), which are electrically coupled to the antennas 306a, 306b. The transmitter drives at least one of the antenna 306a, 306b to transmit excitation signals over a plurality of frequencies. The receiver is coupled to detect response signals returned via at least one of the antenna 306a, 306b.

In some implementations, the wearable device 300 includes one or more processors hardware circuitry) coupled to the receiver and, or transmitter, and operable to process the received response signals. In some implementations, the wearable device 300 employs a processor-based device or system (not visible in FIG. 3) that is distinct and separate from the wearable device 300 to perform the processing. For example, the wearable device 300 includes one or more radios (not visible in FIG. 3) to transmit information to the processor-based device or system, and to receive information from the processor-based device or system. The radios may allow relative short range wireless communications, for example a Bluetooth radio may provide communications with a smartphone or tablet computer carried by or proximate the subject wearing the wearable device 300. The radios may allow relative long range wireless communications, for example a WI-FI radio or cellular communications radio may provide communications with a server or backend computer located remotely from the subject wearing the wearable device 300. Thus, processing can occur on the wearable device 300, can occur on a separate processor-based device or system located proximate to the wearer, or occur on a separate processor-based device or system (e.g., hub or server) located remotely from the wearer.

The wearable device 300 includes at least one indicator (not visible in FIG. 3), for example a display screen, speaker, beeper or other device operable to produce a user perceptible signal, and which can produce a notification representative of a presence or absence of an abnormal condition of the bodily tissue or health of the subject.

Figure 4:
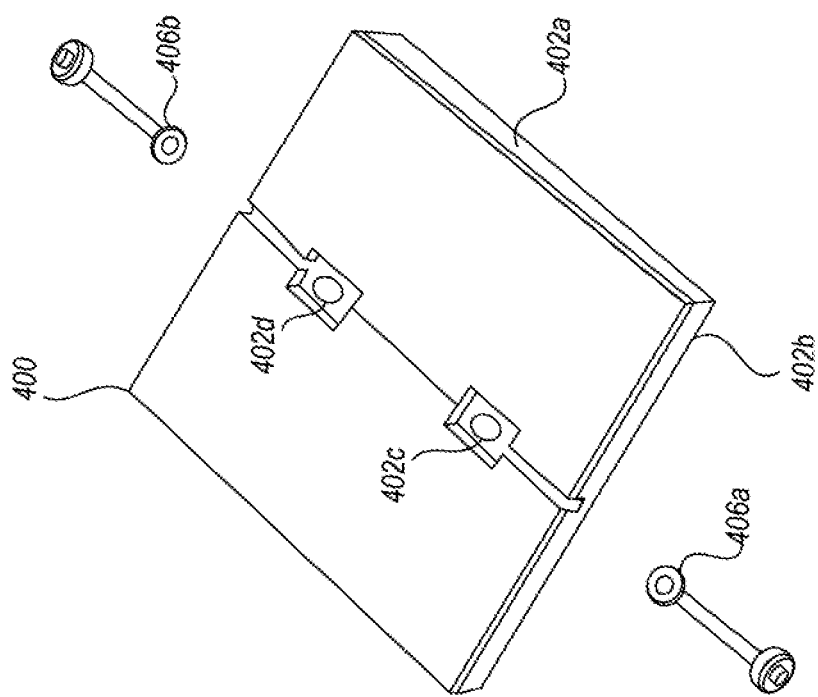
FIG. 4 is an exploded isometric view of an interface of an automated medical diagnostic system comprising a circuit board with a shield layer of material, and a set of antennas mountable to the circuit board, according to at least one illustrated implementation.

FIG. 4 shows an interface 400, according to at least one illustrated implementations.

The interface 400 may take the form of a printed circuit board 402, having one or more layers of electrically insulating material (e.g., FR4) 402a and one or more layers of a metal (e.g., printed or deposited layer, foil, mesh) 402b. The layer of metal 402b can substantially cover the area of the printed circuit board 402 except for regions 402c, 402d (two shown) at which the antennas 406a, 406b will be located. Thus, the interface 400 includes an integral shield, and hence is itself a shield against EMF along undesired paths.

Figure 5:
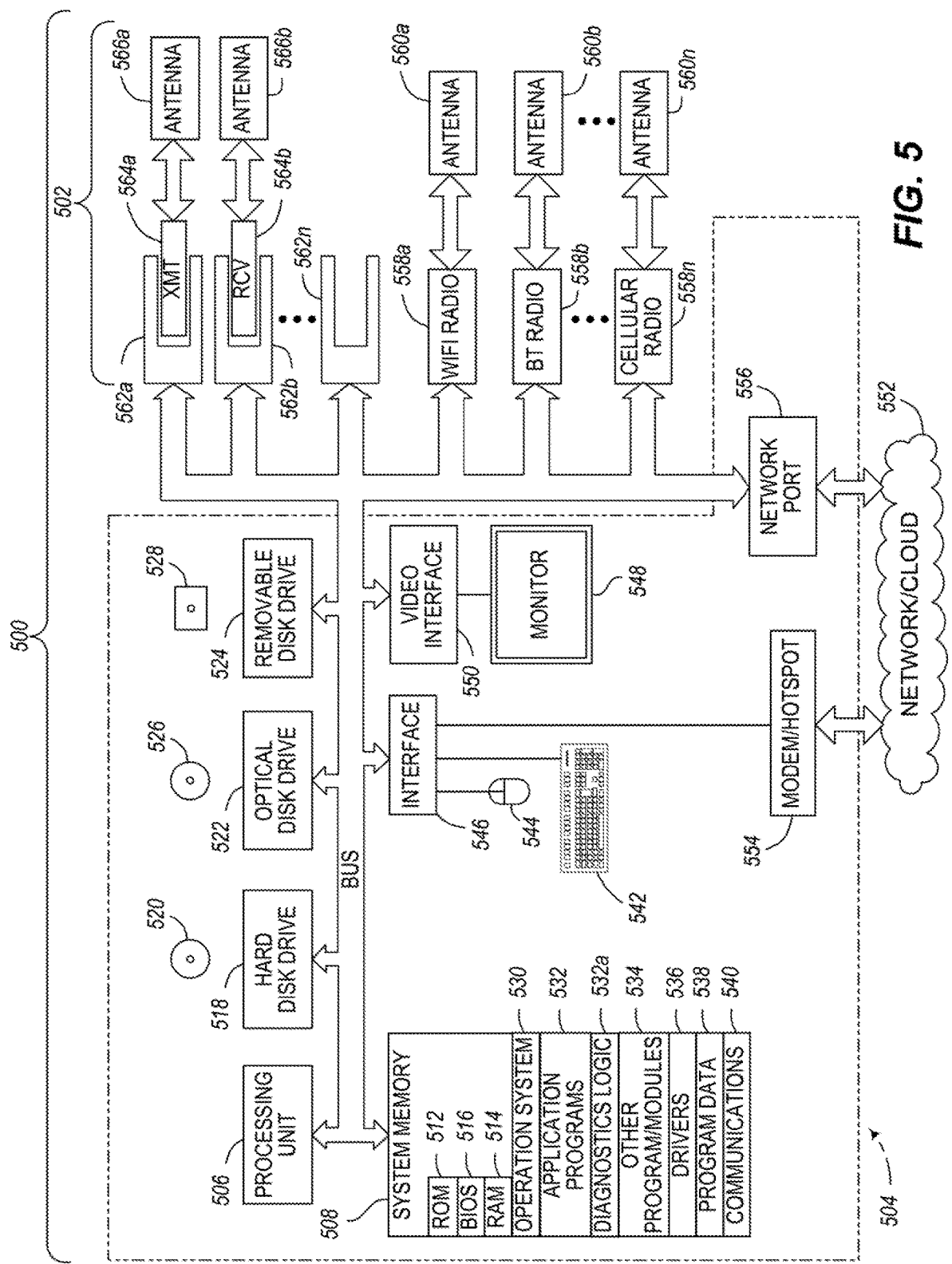
FIG. 5 is a schematic diagram of an automated medical diagnostic system according to one illustrated implementation, the automated medical diagnostic system including a processor system, various transmitters, receivers or transceivers coupled with antennas.

FIG. 5 and the following discussion provide a brief, general description of a suitable automated medical diagnostic system 500 in which the various illustrated embodiments, as well as other embodiments can be implemented. The automated medical diagnostic system 500 can for example implement the automated medical diagnostic system 100 (FIG. 1).

Although not required, some portion of the embodiments will be described in the general context of computer-executable instructions or logic, such as program application modules, objects, functions, procedures or macros being executed by a computer or processor. Those skilled in the relevant art will appreciate that the illustrated embodiments as well as other embodiments can be practiced with other computer- or processor-based system configurations, including handheld devices, multiprocessor systems, microprocessor-based or programmable consumer electronics, personal computers ("PCs"), network PCs, minicomputers, mainframe computers, and the like. The embodiments can be practiced in distributed computing environments where tasks or modules are performed by remote processor-based devices, which are linked through a communications network. In a distributed computing environment, program modules may be located in local and/or remote memory storage devices, for instance in the cloud. Network connections allow for cloud computing and/or cloud storage.

The automated medical diagnostic system 500 includes an interface 502 and a processor-based device or system 504 which is communicatively coupled to the interface 502, and in some implementations to numerous instances of interfaces 502.

The processor-based device or system 504 may take the form of a conventional personal computer (PC) or a wearable computer, which includes one or more processors 506, system memories 508 and system buses 510 that couple various system components including the system memory 508 to the processor 506. The processor-based device or system 504 and its components will at times be referred to in the singular herein, but this is not intended to limit the embodiments to a single system or single components, since in certain embodiments, there will be more than one system or other local or remote networked computing device or multiple instances of any component involved.

The processor 506 may be any logic processor, such as one or more central processor units (CPUs), microprocessors, digital signal processors (DSPs), application-specific integrated circuits (ASICs), field programmable gate arrays (FPGAs), etc.

The processor 506 may take the form of a full microprocessor. Non-limiting examples of commercially available microprocessors include, but are not limited to, an 80x86 or Pentium series microprocessor from Intel Corporation, U.S.A., a PowerPC microprocessor from IBM, a Sparc microprocessor from Sun Microsystems, Inc., a PA-RISC series microprocessor from Hewlett-Packard Company, or a 68xxx series microprocessor from Motorola Corporation, A12 from Apple Computer, or SnapDragon® processor. For example, the processor 506 may take the form of a full microprocessor such as the ATOM™ processor, commercially available from Intel Corporation. The full microprocessor may be communicatively coupled to multiple analog antenna channels, for example via one or more transmitters 564a and, or one or more receivers 564b which may take the form of one or more transceivers.

The system bus 510 can employ any known bus structures or architectures, including a memory bus with memory controller, a peripheral bus, and a local bus. A relatively high bandwidth bus architecture may be employed. For example, a PCI Express™ or PCIe™ bus architecture may be employed, rather than an ISA bus architecture. Some embodiments may employ separate buses for data, instructions and power.

The system memory 508 includes read-only memory ("ROM") 512 and random access memory ("RAM") 514. A basic input/output system ("BIOS") 516, which can form part of the ROM 512, contains basic routines that help transfer information between elements within the processor-based device or system 504, such as during start-up.

The processor-based device or system 504 also optionally includes a hard disk drive 518 for reading from and writing to a magnetic disk 520, an optical disk drive 522 for reading from and writing to removable optical disks 526, and, or a removable disk drive 524 for reading from and writing to removable disks 528. The optical disk 526 can be a CD or a DVD, etc., while the removable magnetic disk 528 can be a magnetic floppy disk or diskette. The hard disk drive 518, optical disk drive 522 and removable disk drive 524 communicate with the processor 506 via the system bus 510. The hard disk drive 518, optical disk drive 522 and removable disk drive 524 may include interfaces or controllers (not shown) coupled between such drives and the system bus 510, as is known by those skilled in the relevant art. Additionally or alternatively, the processor-based device or system 504 may include one or more solid state drives (SSD) (not shown). The drives 518, 522, 524, and their associated computer-readable media 520, 526, 528, provide nonvolatile storage of computer-readable/processor-executable instructions, data structures, program modules and other data for the processor-based device or system 504. Although the depicted processor-based device or system 504 employs hard disk 520, optical disk 526 and removable disk 528, those skilled in the relevant art will appreciate that other types of computer-readable media that can store data accessible by a computer may be employed, such as magnetic cassettes, flash memory cards, RAMs, ROMs, smart cards, etc.

Program modules can be stored in the system memory 508, such as an operating system 530, one or more application programs 532, other programs or modules 534, drivers 536 and program data 538.

The application programs 532 may, for example, include diagnostics logic 532a to perform spectrometry based analysis or medical diagnostics, for example determining a difference (e.g., the gain/loss) between excitation and response signals at each of a number of frequencies, comparing those differences to a set of baseline differences, identifying patterns based on the comparisons, and providing notifications based on identified patterns or lack thereof, as discussed below with reference to FIGS. 6 through 11. The diagnostics logic 532a may, for example, be stored as one or more executable instructions. The diagnostics logic 532a may include logic or instructions to cause antenna(s) 106 (FIG. 1) to transmit wireless excitation signals at each of a plurality of frequencies, receive response signals returned from bodily tissue in response to the excitation signals, and analysis information encoded in the response signals or differences between the excitation and response signals.

The system memory 508 may also include communications programs 540, for example a server and/or a Web client or browser for permitting the processor-based device or system 504 to access and exchange data with other systems such as user computing systems, Web sites on the Internet, corporate intranets, extranets, or other networks as described below. The communications programs 540 in the depicted embodiment is markup language based, such as Hypertext Markup Language (HTML), Extensible Markup Language (XML) or Wireless Markup Language (WML) or Structured Query Language (SQL), and operates with markup languages that use syntactically delimited characters added to the data of a document to represent the structure of the document or to format information. A number of servers and/or Web clients or browsers are commercially available such as those from Mozilla Corporation of California and Microsoft of Washington being HIPAA compliant or not.

While shown in FIG. 5 as being stored in the system memory 508, the operating system 530, application programs 532, other programs/modules 534, drivers 536, program data 538 and server and/or browser 540 can be stored on the hard disk 520 of the hard disk drive 518, the optical disk 526 of the optical disk drive 522 and/or the magnetic disk 528 of the magnetic disk drive 524. A user can enter commands and information into the processor-based device or system 504 through input devices such as a touch screen or keyboard 542 and/or a pointing device such as a mouse 544. Other input devices can include a microphone, joystick, game pad, tablet, scanner, biometric scanning device, etc. These and other input devices are connected to the processor 506 through an interface 546 such as a universal serial bus ("USB") interface, Firewire, and/or optical Firewire interface, that couples to the system bus 510, although other interfaces such as a parallel port, a game port or a wireless interface or a serial port may be used. A monitor 548 or other display device is coupled to the system bus 510 via a video interface 550, such as a video adapter. Although not shown, the processor-based device or system 504 can include other output devices, such as speakers, printers, etc.

The processor-based device or system 504 operates in a networked environment using one or more of the logical connections to communicate with one or more remote computers, servers and/or devices via one or more communications channels, for example, one or more networks 552. These logical connections may facilitate any known method of permitting computers to communicate, such as through one or more LANs and/or WANs, such as the Internet, intranet, cloud and/or extranet. Such networking environments are well known in wired and wireless enterprise-wide computer networks, intranets, extranets, and the Internet. Other embodiments include other types of communication networks including telecommunications networks, cellular networks, paging networks, and other mobile networks.

When used in a WAN networking environment, the processor-based device or system 504 may include a modem or wireless hotspot 554 for establishing communications over a WAN, for instance the Internet. The modem 554 is shown in FIG. 5 as communicatively linked between the interface 546 and the network 552. Additionally or alternatively, another device, such as a network port 556, that is communicatively linked to the system bus 510, may be used for establishing communications over the network 552.

One or more radios, for example WI-FI® radio 558a, Bluetooth® radio 558b, cellular radio 558n and associated antennas 560a, 560b, 560n may be used for establishing wireless communications via WI-FI® networks, Bluetooth® channel, or cellular provider networks. One or more interfaces or ports 556 that are communicatively linked to the system bus 510, may be used for establishing communications over a WAN, LAN, parallel or serial cable, AC wiring (e.g., ZigBee® protocol transceiver), or wirelessly. In some embodiments, the interfaces or ports may take the form of USB ports allowing communication via respective USB cables. Such may allow a variety of equipment to communicate with the processor-based device or system 504. For example, peripheral equipment (not illustrated).

One or more interfaces or slot connectors 562a-562n (collectively 562, only three illustrated) may allow the communicative coupling of plug-in boards 564a, 564b (collectively 564, only two illustrated) to the processor-based device or system 504. There may, for example, be one plug-in board 562 for each antenna 566a, 566b (collectively 566, only two illustrated, each of the antennas 566 and plug-in boards 564 constituting a separate channel. The slot connectors 562 may allow expansion or use with different antenna configurations. The plug-in boards 564 may each carry one or more circuits (e.g., analog and/or digital circuit components) configured to transmit excitation signals from the respective antenna 566 at each of a plurality of frequencies and to monitor the antenna 566 for response signals in response to the excitation signals. For example, the plug-in boards 564 may implement or carry transmitter and, or receiver, and, or transceiver circuits operable in the radio and, or microwave frequency bands of the electromagnetic spectrum.

In a networked environment, program modules, application programs, or data, or portions thereof, can be stored in a server computing system (not shown) or in the cloud. Those skilled in the relevant art will recognize that the network connections shown in FIG. 5 are only some examples of ways of establishing communications between computers, and other connections may be used, including wirelessly.

For convenience, the processor 506, system memory 508, network port 556, interface 546, radios 558 and connector slots 562 are illustrated as communicatively coupled to each other via the system bus 510, thereby providing connectivity between the above-described components. In alternative embodiments of the processor-based device or system 504, the above-described components may be communicatively coupled in a different manner than illustrated in FIG. 5. For example, one or more of the above-described components may be directly coupled to other components, or may be coupled to each other, via intermediary components (not shown). In some embodiments, system bus 510 is omitted and the components are coupled directly to each other using suitable connections.

Figure 6:
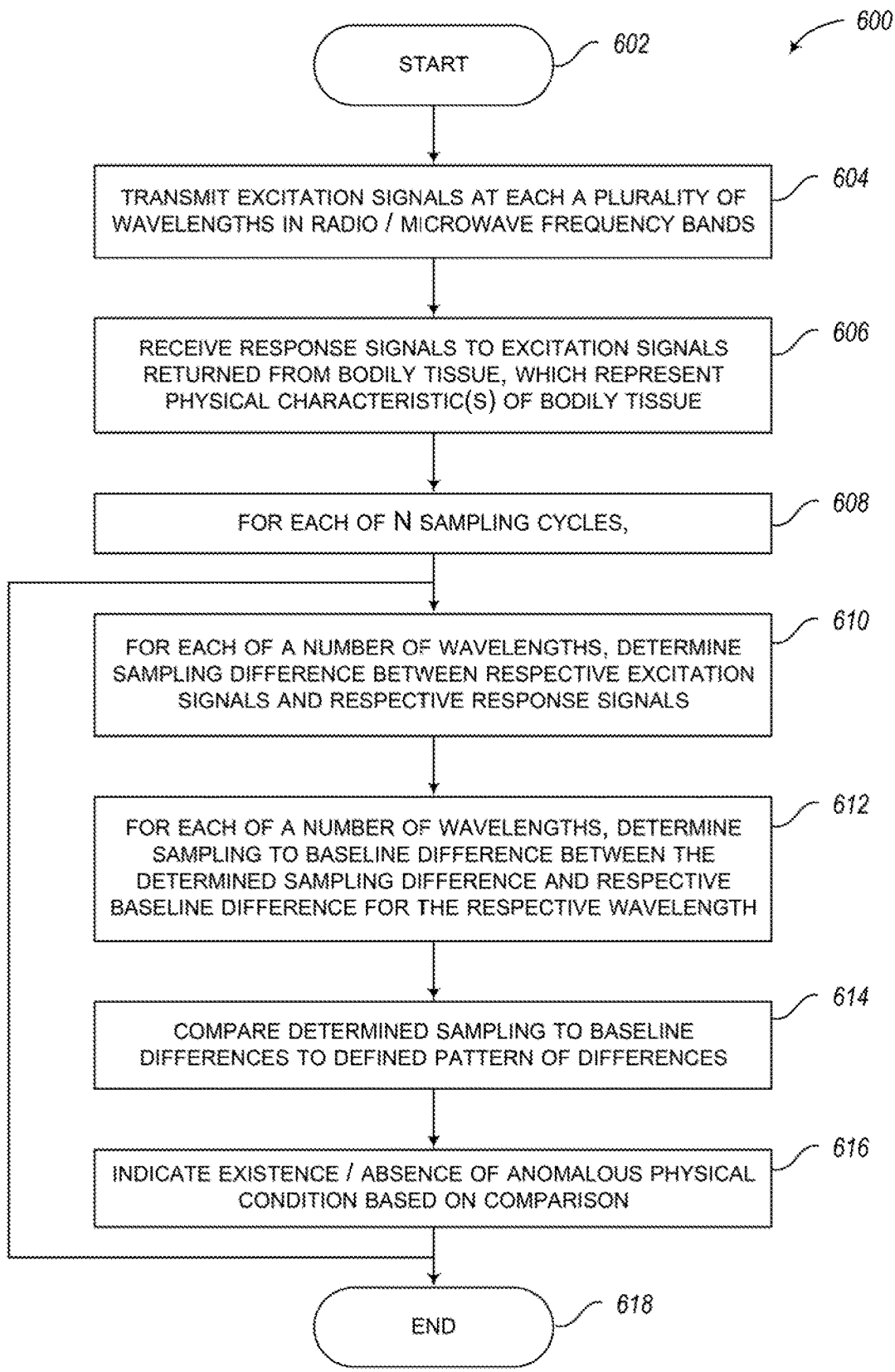
FIG. 6 is a high level flow diagram showing a method of operation of an automated medical diagnostic system, according to at least one illustrated implementation.

FIG. 6 shows a method 600 of operating a health assessment or automated or semi-automated medical diagnostic system, according to one illustrated implementation. The method 600 can, for example, be implemented by the structures of FIGS. 1-5, which includes one or more antennas, transmitters, receivers, and processor-based systems to transmit excitation signals at a plurality of discrete frequencies in non-optical portions of the electromagnetic spectrum to bodily tissue, receive response signals from the bodily tissue, determine a sampling difference, compare the sampling differences to a set of baseline differences, and determine whether particular patterns exist.

The method 600 starts at 602, for example on power ON of one or more components (e.g., transmitter(s), receiver(s), processor-based system), or on invocation of some calling program, routine, subprogram or function.

Optionally, the method 600 may be performed at a first time to establish a baseline, against which information or data collected over subsequent sampling periods is compared. The baseline can be a baseline for the specific subject, for example based on prior sampling of that same subject. The baseline can be a generic baseline, established by sampling a plurality of different subjects. A specific generic baseline may be selected for a subject based on some physical characteristics, for instance age, gender, ethnicity.

At 604, a transmitter coupled or coupleable to at least one antenna and operable to transmit a plurality of excitation signals at each of a plurality of wavelengths in at least one of a radio frequency band and, or, a microwave frequency band of the electromagnetic spectrum via at least one antenna. The transmitter may, for example transmit excitation signals at each of a plurality of frequencies, for instance in equal steps or unequal steps across all or a portion of a desired range or set of frequencies. The transmitter may, for example transmit excitation signals at each of a defined number of frequencies, omitting one or more frequencies in the desired range or set of frequencies or omitting subsets of frequencies. The transmitter may, for example omit transmission of excitation signals at each of a number of frequencies or subsets of frequencies. The transmitter may, for example transmit excitation signals at each of a plurality of frequencies, for instance in unequal steps or unequal steps across all or a portion of a desired range or set of frequencies. For example, previous analysis may indicate that certain frequencies are not indicative of a given health or medical condition. The transmitter skips these frequencies, advantageously allowing shorter delays between transmission of excitation signals, quicker completion of a given cycle through a range of frequencies, and, or faster processing. The particular pattern (e.g., frequencies, order of frequencies, timing between frequencies) may be specific to a given abnormal condition, or to a specific physical characteristic of the bodily tissue that is being assessed (e.g., a first pattern of excitation signals to assess a first physical characteristic of the bodily tissue, a second pattern of excitation signals to assess a second physical characteristic of the bodily tissue, the second physical characteristic different from the second physical characteristic.)

At 606, a receiver coupled or coupleable to at least one antenna and operable to receive a plurality of response signals to the excitation signals which are returned or passed through from the bodily tissue via at least one antenna in response to the excitation signals and which represent at least one physical characteristic of the bodily tissue from which the response signals are returned.

At 608, a processor-based device or system executes one or more sampling cycles, which includes acts 610-616 set out below. The processor-based device or system may take the form of the processor-based device or system 112 (FIG. 1) or the processor-based device or system 504 (FIG. 5).

At 610, the processor-based device or system for each of a number of the plurality of wavelengths, determines a sampling difference between a respective excitation signal and a respective response signal at the respective wavelength. For example, the processor-based device or system may determine an amount of gain or loss (e.g., dB) between an excitation signal at a given frequency and the corresponding response signal that resulted from the excitation signal.

At 612, for each of a number of the plurality of wavelengths the processor-based device or system determines a sampling to baseline difference between the determined sampling difference and a respective baseline difference for the respective wavelength. The baseline difference represents a difference between a respective baseline excitation signal at the respective wavelength and a corresponding baseline response signal at the respective wavelength. Each baseline response signal represents a respective response to the respective baseline excitation signal at the respective frequency for a baseline physical condition of the bodily tissue. As noted the baseline condition can be specific to a subject, or may be generic, that is representing a sampling across multiple subjects. The baseline differences for each of a plurality of frequencies may have been previously established and stored in one or more data structures in memory of the processor-based device or system. As described elsewhere herein, the processor-based device or system may optionally determine whether at least some of the determined sampling to baseline differences are within a range defined by a lower threshold value and an upper threshold value.

At 614, the processor-based device or system compares at least some of the determined sampling to baseline differences to defined pattern of differences. The defined pattern of differences may be representative of a specific subject (e.g., specific individual) or representative of a plurality of subjects (e.g., two or more, and preferable a statistical significant sampling of individuals).

In some implementations, a pattern representative of a single physical characteristic (e.g., presence or absence of a particular substance in the bodily tissue) may be sufficient to assess the presence or absence or likelihood of an abnormal condition. In other implementations, a pattern representative of a two or more physical characteristic (e.g., presence or absence of a particular substance in the bodily tissue) is advantageously used to assess the presence or absence or likelihood (e.g., 47% likelihood) of a single abnormal condition (e.g., developing flu conditions within a given time period (e.g., 24 hours), or even of multiple abnormal conditions.

At 616, the processor-based device or system cause an indication to be provided of an existence or absence of an anomalous physical condition based on the comparison of at least some of the determined sampling to baseline differences to defined pattern of differences. The indication can, for example, take the form of a visual and/or aural alert. Such can be provided via a display monitor, speakers and/or a heads up or head-worn device, e.g., a virtual reality or augmented reality headset. If detected, the existence of an anomalous physical condition may be electronically recorded to nontransitory computer- or processor-readable media.

The method 600 terminates at 618, for example until invoked again. In some implementations, the method 600 may be executed repeatedly, even continuously, or periodically or aperiodically. The method 600 can be implemented as multiple threads, for example via a multi-threaded processor.

Figure 7:
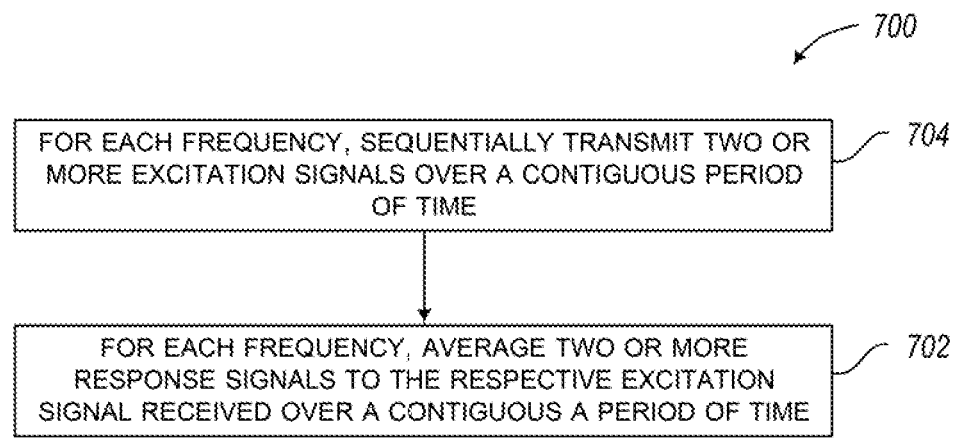
FIG. 7 is low level a flow diagram showing a method of operation of an automated medical diagnostic system, according to at least one implementation, the method useful in performing the method of FIG. 6.

FIG. 7 shows a method 700 of operating a health assessment or automated medical diagnostic system, according to one illustrated implementation. The method 700 can, for example, be implemented by the structures of FIG. 1 and/or FIG. 5. The method 700 can, for example, be implemented or performed as part of implementing or performing the method 600 (FIG. 6).

At 702, for each of the frequencies of excitation signal, the transmitter sequentially transmit two or more excitation signals at the respective frequency over a period of time. Thus, the transmitter may, for example step through frequencies (e.g., 10 MHz steps) and at each step or period emit two or more excitation signals. Such may advantageously improve resolution or accuracy of the spectroscopic analysis.

At 704, for each of the frequencies at which the excitation signals are transmitted, the receiver may average two or more response signals to the respective excitation signal at the respective frequency which are returned from the bodily tissue over a period of time. Such may advantageously improve resolution or accuracy of the spectroscopic analysis.

While method 700 includes transmitting two or more excitation signals at each selected frequency, this act can be omitted from the method 700, and the method 700 may consist of averaging two or more response signals to the excitation signals at each of the selected frequencies.

While method 700 includes averaging two or more response signals to the excitation signals at each of the selected frequencies, this act can be omitted from the method 700, and the method 700 may consist of transmitting two or more excitation signals at each selected frequency.

The method 700 may terminates, for example until invoked again. In some implementations, the method 700 may be executed repeatedly, even continuously, or periodically or aperiodically. The method 700 can be implemented as multiple threads, for example via a multi-threaded processor.

Figure 8:
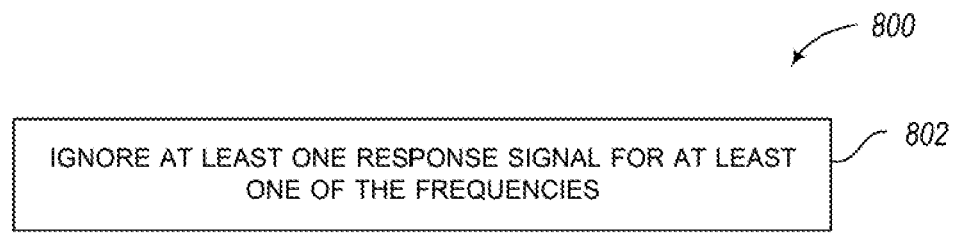
FIG. 8 is low level a flow diagram showing a method of operation of an automated medical diagnostic system, according to at least one implementation, the method useful in performing the method of FIG. 6.

FIG. 8 shows a method 800 of operating a health assessment or automated medical diagnostic system, according to one illustrated implementation. The method 800 can, for example, be implemented by the structures of FIG. 1 and/or FIG. 5. The method 800 can, for example, be implemented or performed as part of implementing or performing the method 600 (FIG. 6).

At 804, the receiver ignores at least one response signal to the respective excitation signal for at least one of the frequencies. For example, previous analysis may indicate that certain frequencies are not indicative of a given health or medical condition. The receiver ignores these frequencies, advantageously allowing faster processing, and for instance shorter delays between transmission of excitation signals.

The method 800 terminates, for example until invoked again. In some implementations, the method 800 may be executed repeatedly, even continuously, or periodically or aperiodically. The method 800 can be implemented as multiple threads, for example via a multi-threaded processor.

FIG. 9 shows method 900 of operating a health assessment or automated medical diagnostic system, according to one illustrated implementation. The method 900 can, for example, be implemented by the structures of FIG. 1 and/or FIG. 5. The method 900 can, for example, be implemented or performed as part of implementing or performing the method 600 (FIG. 6).

At 902, the transmitter transmits the plurality of excitation signals at each of the plurality of discrete frequencies in equal steps from a first frequency to a second frequency. For example, the transmitter may transmit excitations signals in equal steps (e.g., 10 MHz) from a first frequency of approximately 35 MHz to a second frequency. Alternatively, the transmitter may transmit excitations signals in unequal steps from a first frequency of approximately 35 MHz to a second frequency. For example, the transmitter may transmit excitations signals in equal steps (e.g., 10 MHz) from a first frequency to a second frequency of approximately 2500 MHz. Alternatively, the transmitter may transmit excitations signals in unequal steps from a first frequency to a second frequency of approximately 2500 MHz. For example, the transmitter may transmits the plurality of excitation signals at each of the plurality of discrete frequencies in equal steps (e.g., 10 MHz) from 350 MHz to 2500 MHz. Alternatively, the transmitter may transmits the plurality of excitation signals at each of the plurality of discrete frequencies in unequal steps from 350 MHz to 2500 MHz.

The method 900 ends, for example until invoked again. In some implementations, the method 900 may be executed repeatedly, even continuously, or periodically or aperiodically. The method 900 can be implemented as multiple threads, for example via a multi-threaded processor, and can be combined in all or in part with the other workflows or methods described herein.

FIG. 10 shows a method 1000 of operating a health assessment or automated medical diagnostic system, according to one illustrated implementation. The method 1000 can, for example, be implemented by the structures of FIG. 1 and/or FIG. 5. The method 1000 can, for example, be implemented or performed as part of implementing or performing the method 600 (FIG. 6).

At 1002, the transmitter transmits the plurality of excitation signals at each of the plurality of discrete frequencies in a set of frequencies in equal steps for each of one or more subsets of frequencies in the set of frequencies, and skips one or more frequencies between the subsets of frequencies. Alternatively, the transmitter transmits the plurality of excitation signals at each of the plurality of discrete frequencies in a set of frequencies in unequal steps for each of one or more subsets of frequencies in the set of frequencies, and skips one or more frequencies between the subsets of frequencies. The transmitter skips these frequencies advantageously allowing shorter delays between transmission of excitation signals, quicker completion of a given cycle through a range of frequencies, and, or faster processing.

FIG. 11 shows a method 1100 of operating a health assessment or automated medical diagnostic system, according to one illustrated implementation. The method 1100 can, for example, be implemented by the structures of FIG. 1 and/or FIG. 5. The method 1100 can, for example, be implemented or performed as part of implementing or performing the method 600 (FIG. 6).

At 1102, the transmitter transmits the plurality of excitation signals at each of the plurality of discrete frequencies in a set of frequencies, and skips one or more frequencies associated with one or more natural resonance frequencies of water. Alternatively, one or more natural resonance frequencies of water may be particularly indicative of certain abnormalities (e.g., high blood sugar), and thus frequencies other than natural resonance frequencies of water and, or those close to the natural resonance frequencies of water, may be ignored. It has been noted that bodily tissue typically comprises a substantial amount of water, and water tends to have some specific characteristic responses at certain natural frequencies and harmonics thereof. The transmitter skips these frequencies advantageously allowing shorter delays between transmission of excitation signals, quicker completion of a given cycle through a range of frequencies, and, or faster processing.

Figure 12:
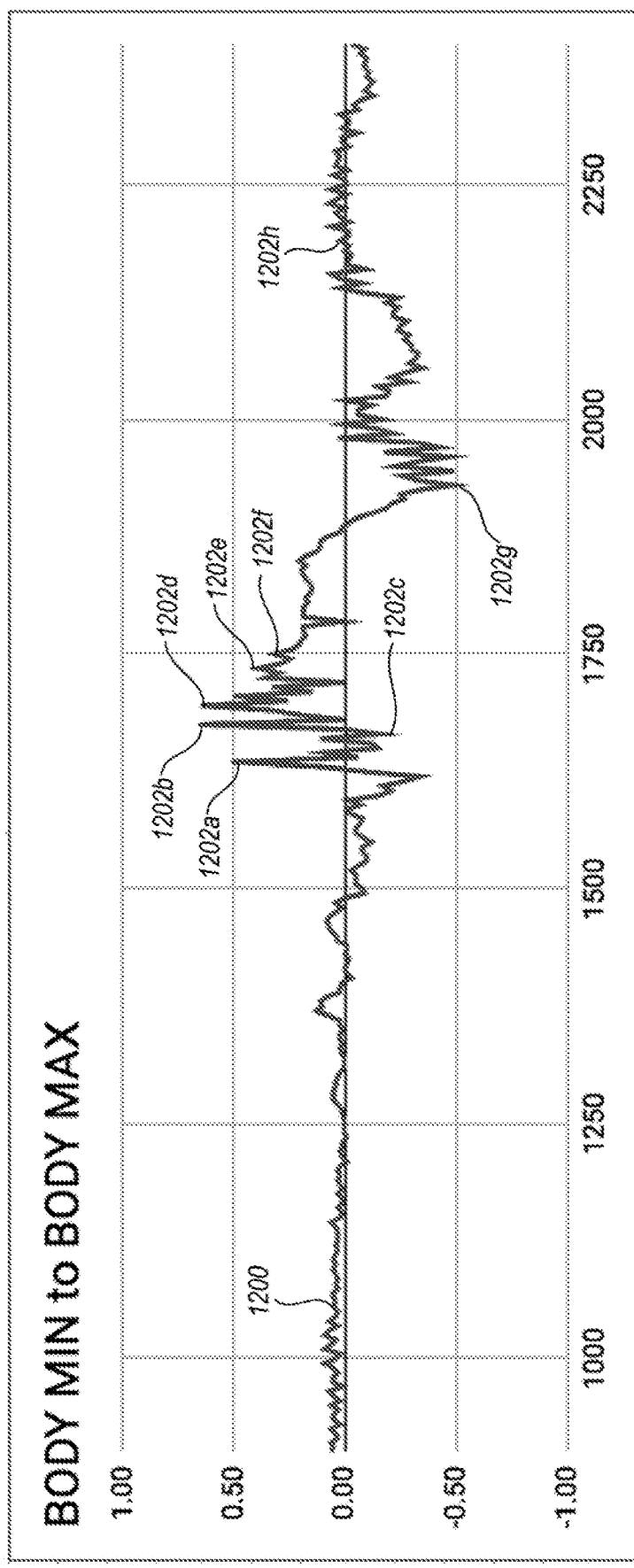
FIG. 12 is graph showing a difference between a sampling difference at a respective excitation frequency and a baseline difference at the respective excitation frequency, for each of a number of a plurality of wavelengths, according to one illustrated example.

FIG. 12 is a graph showing a plot 1200 of a difference between a sampling difference at a respective excitation frequency and a baseline difference at the respective excitation frequency, for each of a number of a plurality of wavelengths, according to one illustrated example. It is noted that equipment setup may or may not be a determinant to the frequency responses of glucose and other elements (e.g., response frequencies may change depending on the construction of the equipment because ultimately the equipment is included in the frequency response).

As noted, the baseline difference can be a difference (e.g., gain/loss), (plotted along the X-axis) between an excitation signal at a given frequency (plotted along the Y-axis) and the corresponding response signal that results from the respective excitation signal at the given frequency, captured or measured at a baseline condition. Differences can, for example, be represented in dB or as a percentage. As also noted, the baseline condition may be a condition of the subject at a previous time. Thus, the baseline may be specific to the subject. Alternatively, the baseline condition may a condition of a plurality of subjects at a previous time, which may in some instances be characterized as a normal condition, or even a healthy condition or a desired condition. Thus, the baseline may be non-specific to the subject. Even when non-specific to the subject, the baseline may be representative of other subjects who share one or more physical characteristics with the subject under examination or being subjected to diagnosis.

As noted, the sampling difference can be a difference (e.g., gain/loss) between an excitation signal at a given frequency and the corresponding response signal that results from the respective excitation signal at the given frequency, captured or measured at a time at which the subject is being assessed (e.g., current time) and during which the subject is in a current condition.

As illustrated, the plot 1200 includes a number of characteristic peaks 1202a, 1202b, 1202c, 1202d, 1202e, 1202f, 1202g. In some instances, one or more of the peaks may be considered outside an expected or reasonable threshold or range, and consequently ignored. Only peaks with some minimum threshold may be employed, for instance peaks indicative of at least a 35% difference between the sampled difference the baseline difference. Also for example, one or more peaks 1202f may be represent too large a difference between the sampled difference and the baseline difference to be considered as reliable. Also for example, one or more peaks 1202g may be considered too small a difference between the sampled difference and the baseline difference to be considered reliable, for instance due to such small differences being more highly sensitive to noise. Peaks around the natural resonance frequencies of water may also be treated as suspect, and ignored in the analysis.

Some implementations may include initially identifying one or more distinctive or characteristics frequencies for a particular substance (e.g., glucose, alcohol) to be tested. The distinctive or characteristics frequencies being frequencies at which the particular substance (e.g., glucose, alcohol) being tested for exhibit a marked or characteristic difference (e.g., inflection point, marked difference in rate of change) from other substances the tissue. In such implementations, an initial screening of one or more subjects at various frequencies across a wide spectrum may be performed, for example emitting radio and/or microwave signals via a first antenna either continuously across the spectrum, or discrete frequencies across the spectrum (e.g., at 1 MHz or 5 MHz steps), and collecting via a second antenna return signals returned from the tissue. The substance may also be measured from the subjects using some generally accepted testing protocol, e.g., glucose test strips, breathalyzer). The results of the standard testing may be used to find or identify correlations with the various characteristics (attenuation) of the collected return signals. Those correlations may, for example, correspond to a subset of points of inflection in the collected return signal, which different from points of inflection is return signals of the given piece of tissue but without the substance that is subject to the testing. Thus, a return signal from a piece of tissue with a given amount or percentage of a substance subject to testing may have a set of inflection points than the inflection points of a return signal from the piece of tissue without the substance subject to testing.

At least one implementation, the system may employ a rate of change between "neighboring" frequencies at one of more distinctive or characteristics frequencies. For example, a difference between neighboring frequencies about a given frequency may be distinctive or characteristics of a presence or absence of a given substance or even a percentage of the substance. The rate of change or other characteristic may be represented in dB, as a difference or attenuation of the collected return signal, for example relative to an excitation or transmitted signal. In some implementations, a first set of values corresponding or representative of response signals or differences between response signals and excitation signals at a first plurality of frequencies may be collected and summed. A second set of values corresponding or representative of response signals or differences between response signals and excitation signals at a second plurality of frequencies may be collected and summed, where the frequencies of the second plurality of frequencies are each a neighboring frequencies of a respective frequencies of the first plurality of frequencies. A neighboring frequency or frequencies of a respective frequency may be a frequency within a defined range of the respective frequency, e.g., within 1 MHz, within 5 MHz, within +/−5 MHz at 1 MHz increments of the respective frequency (e.g., principal excitation frequency). The range may be selected based on a desired level of confidence that is desired in the results. A difference between the sums may then be determined. A rate of change between neighboring frequencies may exhibit a linear relationship, which may, for instance be representative of an absolute value for glucose in the blood. In some applications, e.g., blood alcohol, a raw amplitude may be employed instead of the difference between values at neighboring frequencies.

Various implementations may advantageously employ scattering parameters or S-parameters ($S_{11}$; $S_{12}$; $S_{21}$, $S_{22}$) of a scattering matrix or S-matrix to represent the associated electromagnetic field, for instance representing gain, return loss, voltage standing wave ratio (VSWR), and/or reflection coefficient.

While generally discussed in terms of frequency, the term frequency as used herein and in the claims includes not only frequencies but also and harmonics and/or derivatives of the frequencies, whether expressed in terms of frequencies or wavelengths.

Figure 13:
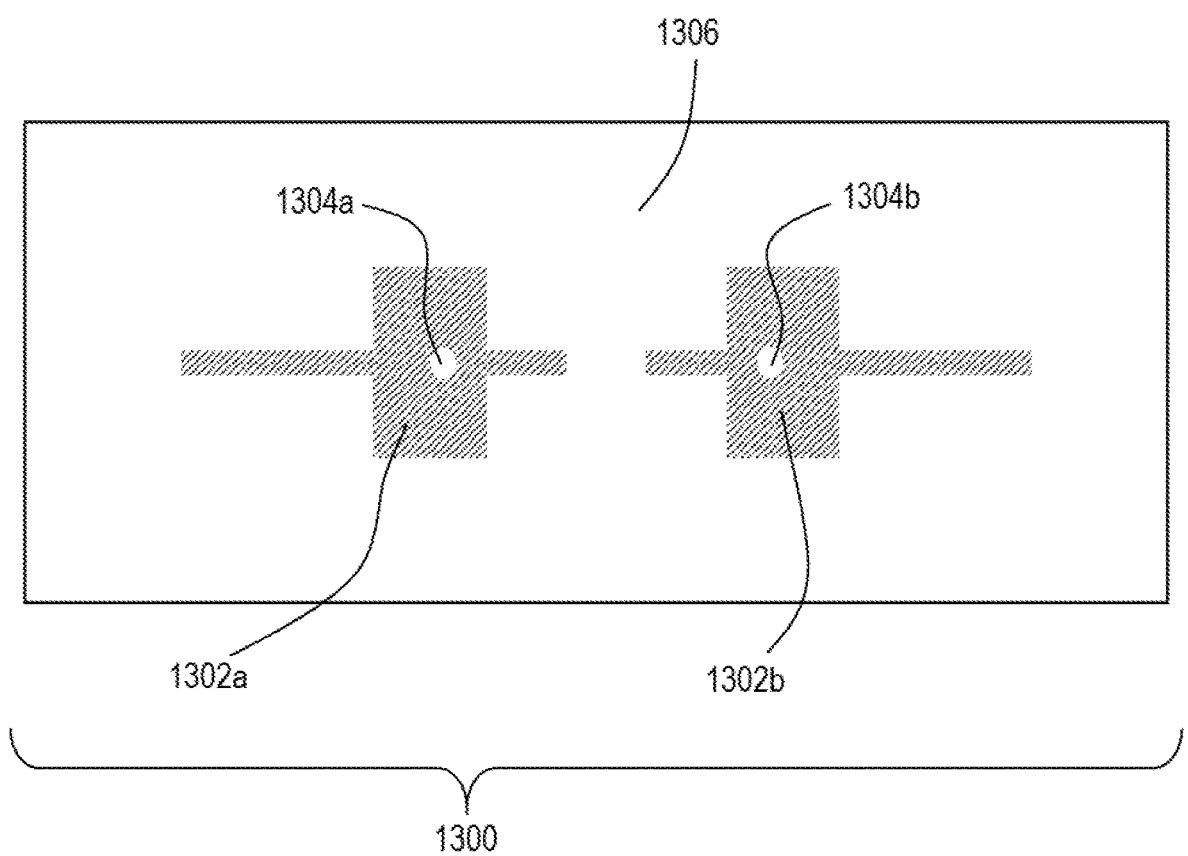
FIG. 13 is a top plan view of an antenna circuit board that includes a circuit board and an antenna, according to at least one illustrated implementation.

FIG. 13 is a top plan view of an antenna circuit board 1300, according to at least one illustrated implementation.

In particular, FIG. 13 shows an antenna shape for the test device or sensor system described herein. The test device or sensor system includes an antenna circuit board 1300, constructed of a copper trace or pattern that forms antenna 1302a, 1302b on an FR4 epoxy printed circuit substrate 1306. The test device or sensor system includes a signal generation and collection system, comprised of a modified Keysight N5171B signal generator and modified Keysight N1913A power meter (Keysight Technologies, Santa Rosa, Calif.). The antenna 1302*a*, 1302*b* are coupled to a signal generation and collection system via connection points or nodes 1304*a*, 1304*b*.

The test device or sensor system was tested via volunteer trials for blood glucose and for blood alcohol, and the various results illustrated in FIGS. 14-19, described below.

Volunteer Trial—Glucose Tracking

This system was tested on a volunteer and the results compared to a U.S. Food and Drug Administration approved transcutaneous continuous blood glucose monitor. On the day of testing, a volunteer was required to forgo food in the morning and then be monitored at a trial facility for approximately 3 hours. Once at the facility, the volunteer was fitted with an Abbott FreeStyle Libre continuous glucose monitoring system (Abbott Laboratories, Abbott Park, Ill.) and required to have a resting blood glucose value of between 80 and 100 mg/dL before testing would begin. The volunteer then placed their forearm onto the armrest of a chair that was fitted with the sensor antenna illustrated in FIG. 13 and coupled to the signal generation and collection system described with reference to FIG. 13. After about 10 minutes of baseline data collection, the volunteer was given a moderate amount of food to eat. Using the FreeStyle Libre data, the volunteer was monitored throughout the procedure to ensure that the volunteer never had excessively high or low blood glucose values. About 2 hours after which testing began, the volunteer ate another small amount of food. Testing was completed after three hours of monitoring.

Glucose values resulting from the test sensor signals, were calculated at 2.5 minutes intervals using the S11 values at ten different frequencies; five of which represent local signal minimums and five of which represents local signal maximums. The frequencies used were 1.001, 1.071, 1.138, 1.200 and 1.260 GHz and 1.035, 1.098, 1.161, 1.223 and 1.285 GHz at minimums and maximums respectively. Furthermore, the sensor signal was time averaged since multiple frequencies may be interrogated within just a few seconds in order to remove signal noise. Equation 1 provides the formula from which the test sensor signal was computed.

Sensor value=(MAX 1.035+MAX 1.098+MAX 1.161+MAX 1.223+MAX 1.285)−(MIN 1.001+ MIN 1.071+MIN 1.138+MIN 1.200+MIN 1.260)

Figure 14:
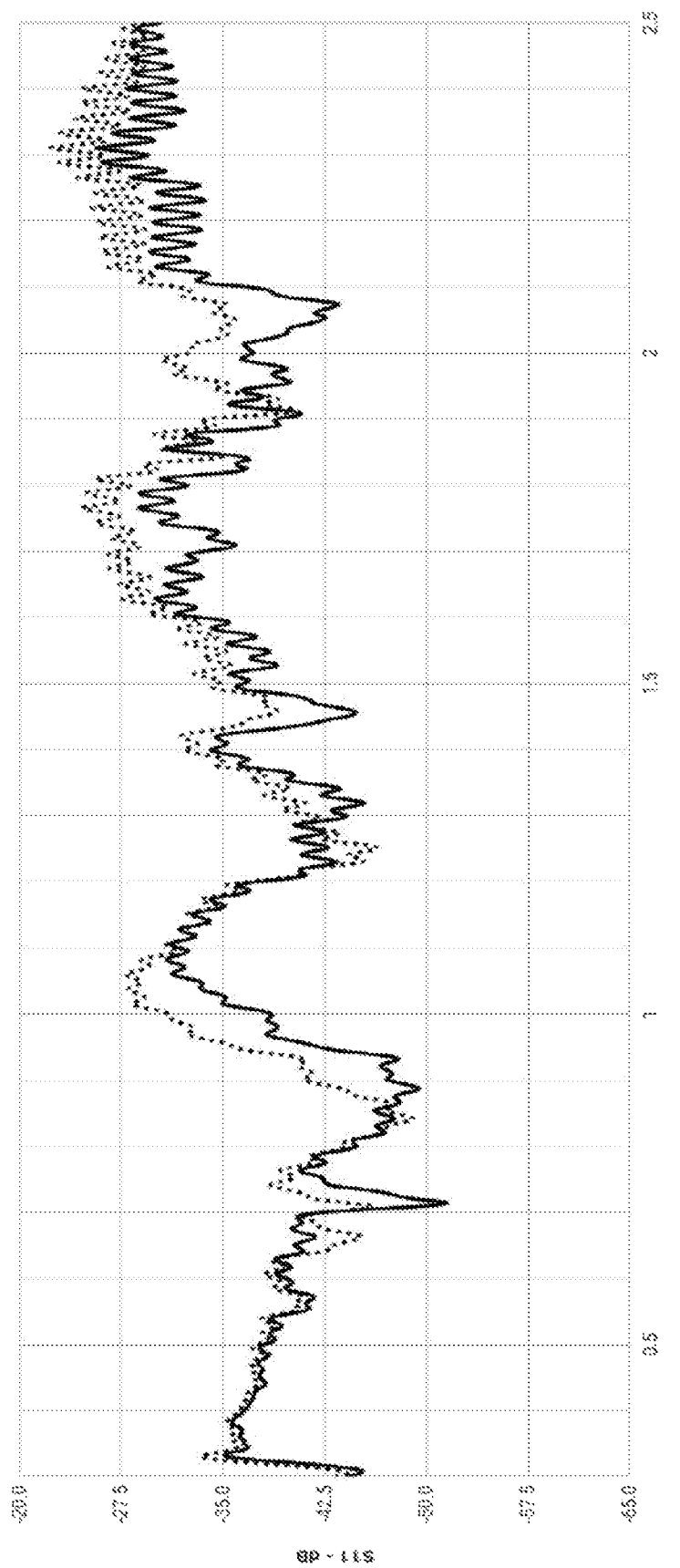
FIG. 14 is a graph that shows a test sensor's S11 signal (dB) response to distilled water (dashed line) and a glucose solution (solid line).

Equation 1 Formula used to calculate a sensor value from local maxima and minima values in the frequency spectra FIG. 14 is a graph that shows a test sensor's S11 signal (dB) response to distilled water (dashed line) and a glucose solution (solid line).

In particular, FIG. 14 illustrates a comparative example of an S11 reflectance signal obtained by the test device or sensor system of FIG. 13 from distilled water and from a glucose solution of approximately 500 mg/dL. The data was collected in 5 MHz increments between 0.30 GHZ and 2.50 GHz.

Figure 15:
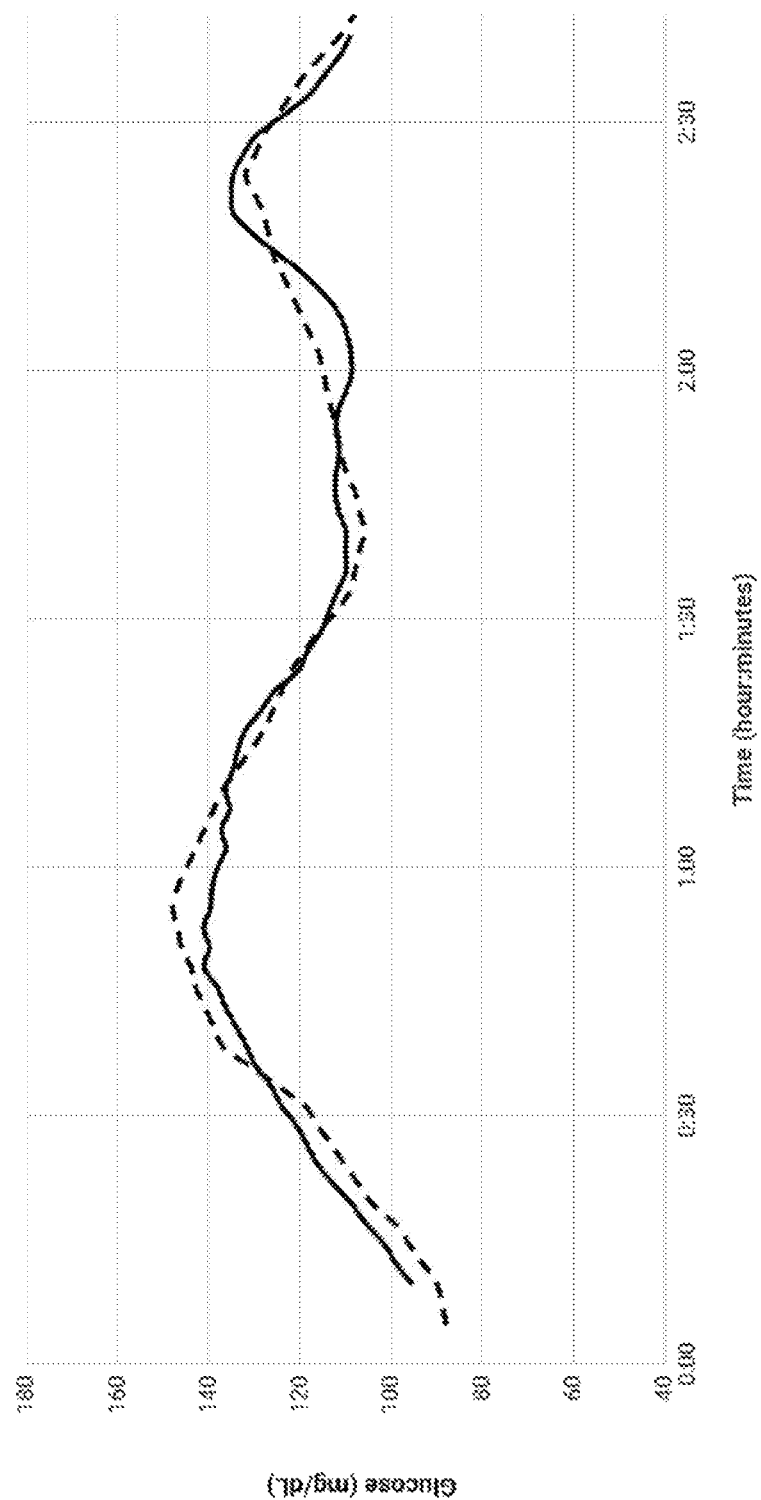
FIG. 15 is a graph that shows glucose concentration measurements over time for a volunteer, measured via a FreeStyle Libre continuous glucose monitor (broken line) and via a test device described herein (solid line).

FIG. 15 is a graph that shows glucose concentration measurements over time for a volunteer, measured via a FreeStyle Libre continuous glucose monitor (broken line) and via the test device or sensor system of FIG. 13 (solid line).

Figure 16:
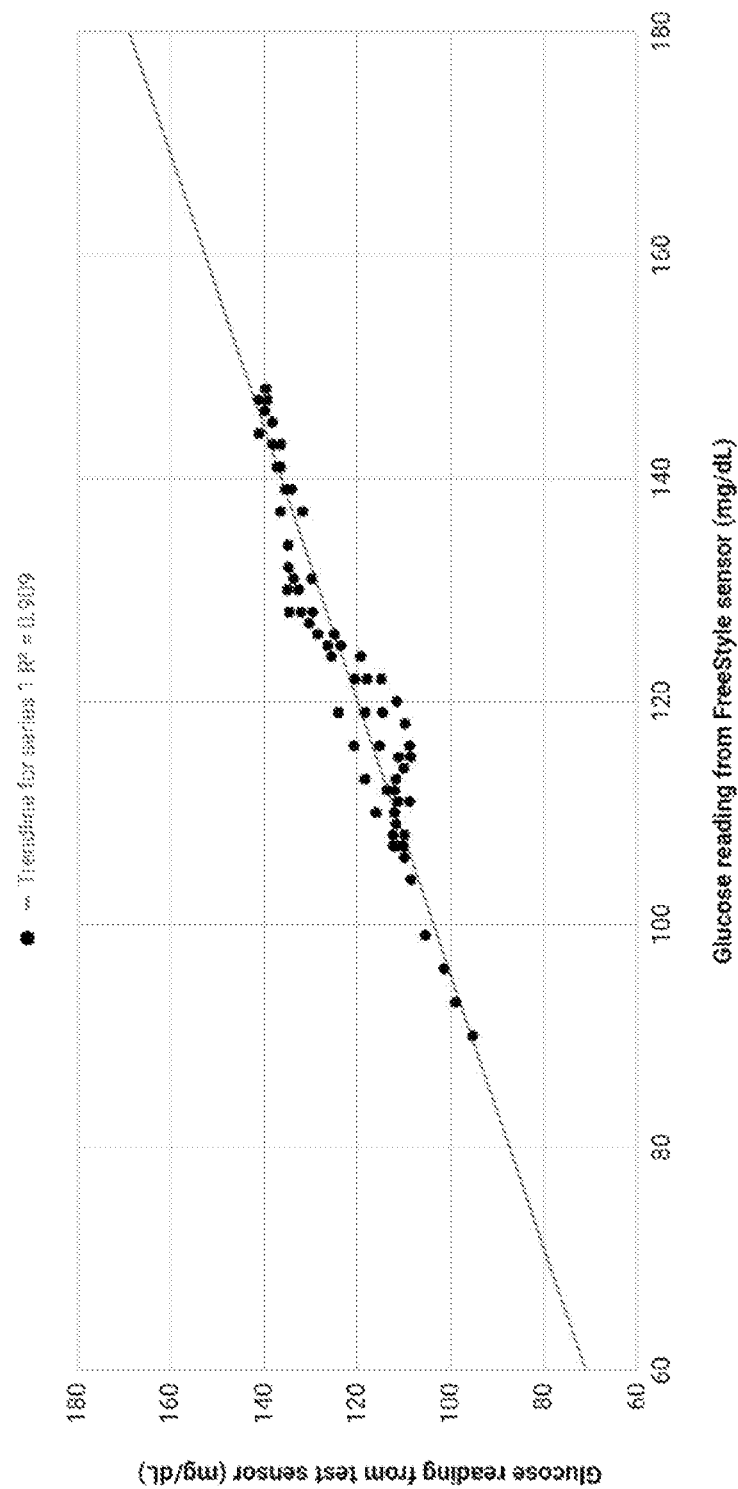
FIG. 16 is a graph that shows a correlation between blood glucose values measured by the FreeStyle sensor and blood glucose values measured by test device described herein, over the 3 hour volunteer study as illustrated in FIG. 15.

FIG. 16 is a graph that shows a correlation between blood glucose values measured by the FreeStyle sensor and blood glucose values measured by the test device or sensor system of FIG. 13, over the 3 hour volunteer study as illustrated in FIG. 15.

Figure 17:
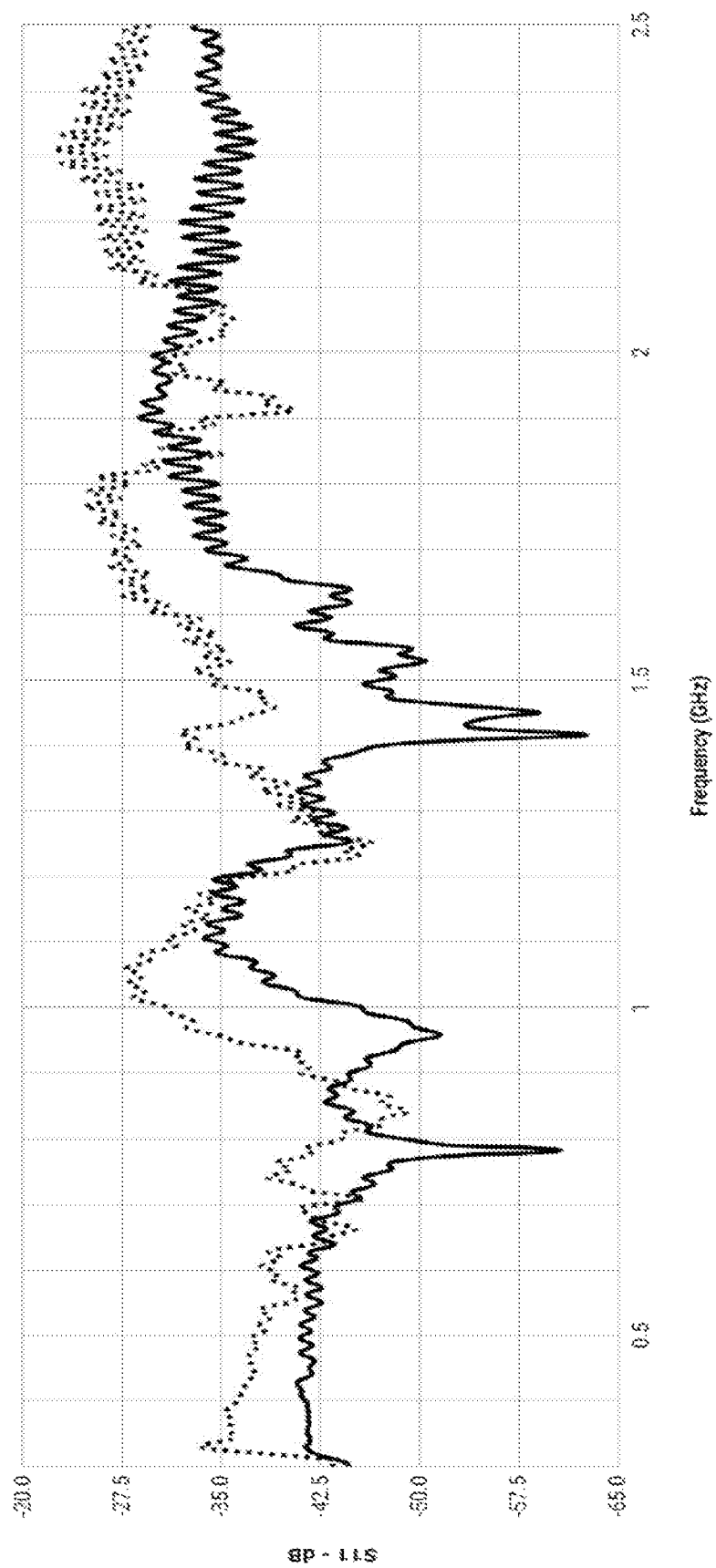
FIG. 17 is a graph that shows a signal (dB) response of a test device described herein to distilled water (broken line) and to an ethanol solution (solid line).

Volunteer Trial—Ethanol Tracking A comparative example of the S11 reflectance signal obtained from distilled water and an ethanol solution of approximately 40% by volume are shown in FIG. 17. The sensor antenna and system hardware are the same as described for the glucose testing example.

The test device or sensor system of FIG. 13 was tested on a volunteer and the results compared to a professional law enforcement breathalyzer. On the day of testing, a volunteer was required to forgo food in the morning and then be monitored at a trial facility for approximately 3 hours. Once at the facility, the baseline level of blood alcohol was measured with a BACtrack S80 breathalyzer (BACtrack Breathalyzers/KHN Solutions Inc., San Francisco, Calif.). The volunteer then placed their forearm onto the armrest of a chair that was fitted with the sensor antenna illustrated in FIG. 13 and coupled to the signal generation and collection system described with reference to FIG. 13. After about 10 minutes of baseline data collection, the volunteer was given an amount of alcohol to drink. The volunteer's blood alcohol level was recorded every 3 to 5 minutes with both the breathalyzer and the test device or sensor system of FIG. 13. Testing was completed after three hours of monitoring.

Unlike the glucose testing results, blood alcohol levels were calculated using only a single frequency.

FIG. 17 is a graph that shows a signal (dB) response of a test device described herein to distilled water (broken line) and to an ethanol solution (solid line). The data was collected in 5 MHz increments between 0.30 GHZ and 2.50 GHz.

Figure 18:
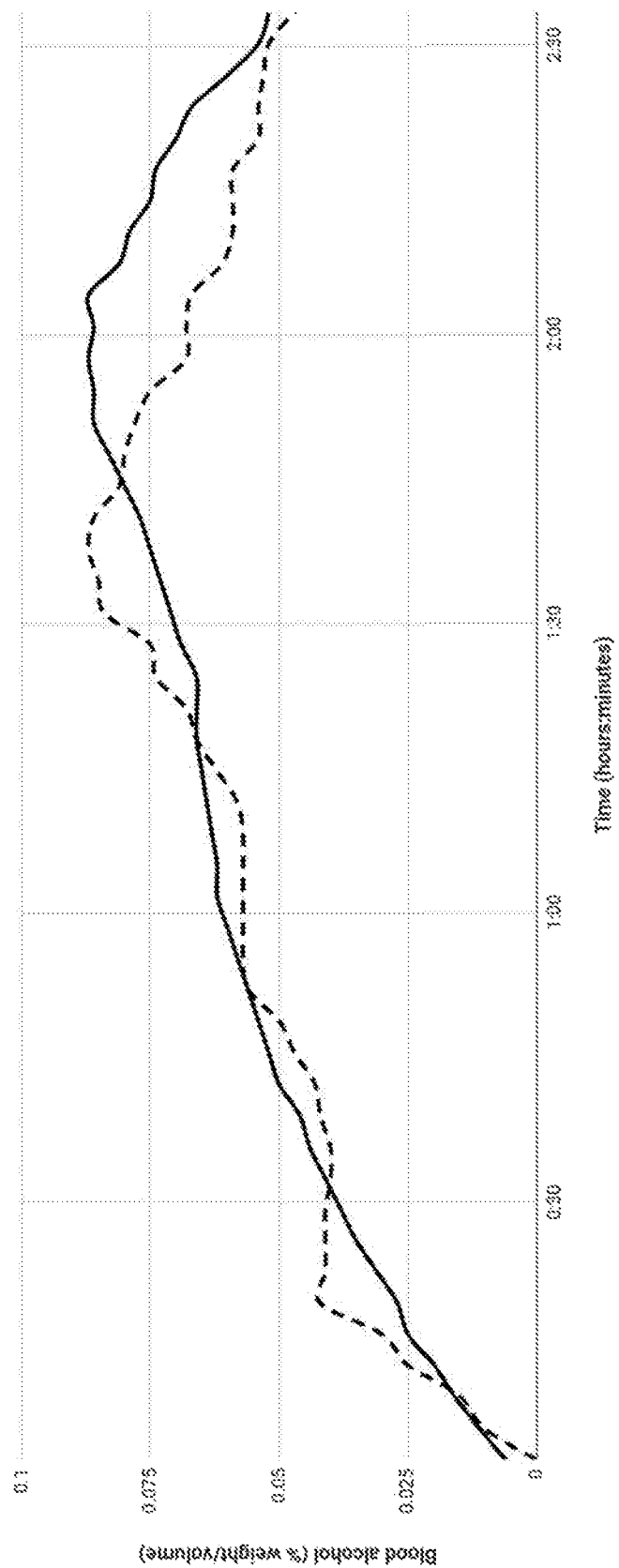
FIG. 18 is a graph that shows a blood alcohol concentration over time for a volunteer as measured using a breathalyzer (broken line) and as measured via a test device described herein (solid line).

FIG. 18 is a graph that shows a blood alcohol concentration over time for a volunteer as measured using a breathalyzer (broken line) and as measured via a test device described herein (solid line).

Figure 19:
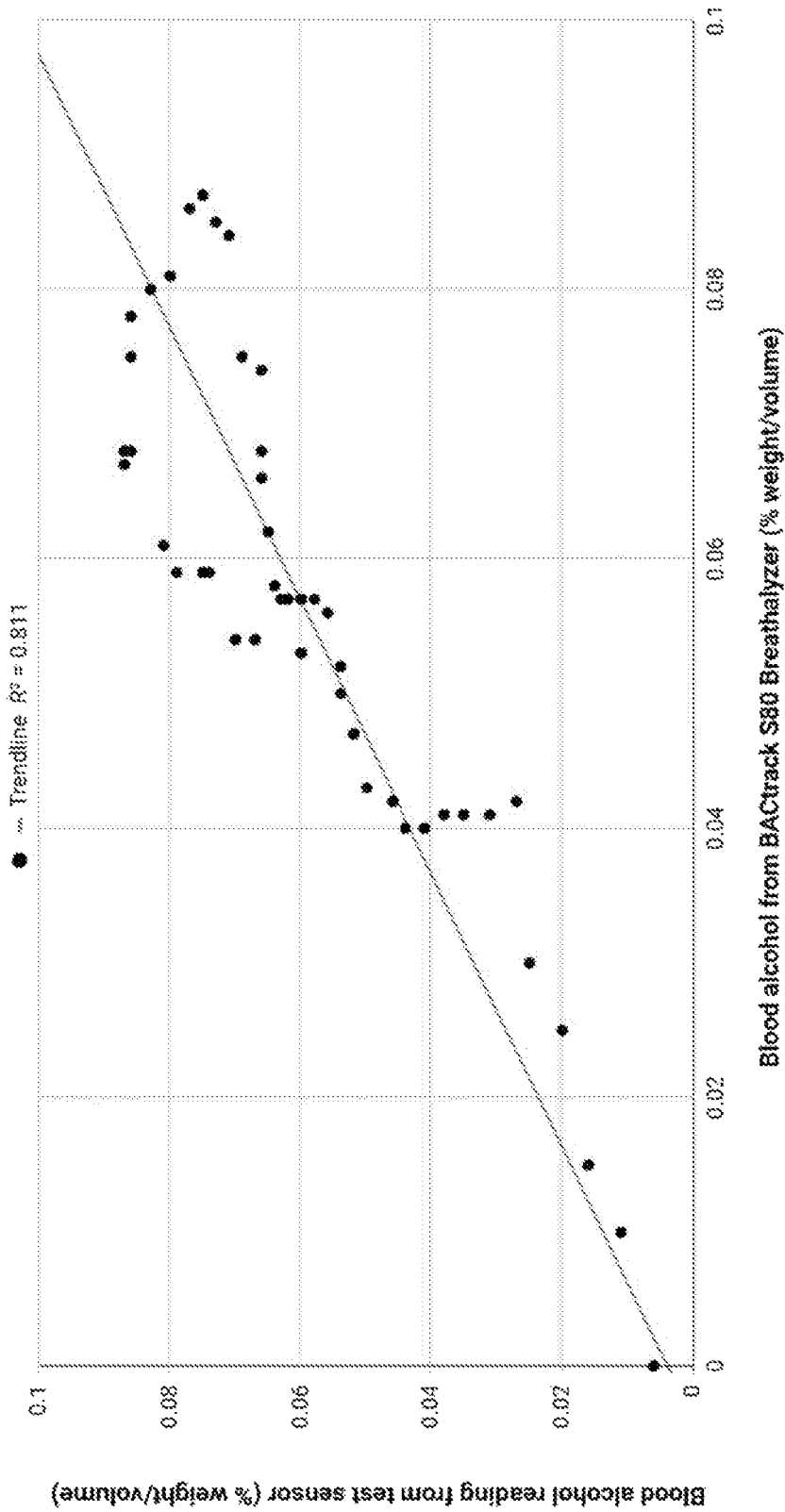
FIG. 19 is a graph that shows a correlation between blood alcohol values measured by a breathalyzer and a test device described herein over the 3 hour volunteer study as illustrated in FIG. 18.

FIG. 19 is a graph that shows a correlation between blood alcohol values measured by a breathalyzer and a test device described herein over the 3 hour volunteer study as illustrated in FIG. 18.

As used herein and in the claims, the term bodily tissue includes the tissue, whether blood or non-blood tissue (e.g., skin or dermis), of any variety of animals, including but not limited to all mammals including humans, reptiles, birds, etc.

Also for instance, the foregoing detailed description has set forth various embodiments of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Various exemplary methods or processes are described. It is noted that these exemplary methods or processes may include additional acts and/or may omit some acts. In some implementations, the acts of the various exemplary methods or processes may be performed in a different order and/or some acts may be executed or performed concurrently.

In addition, those skilled in the art will appreciate that the mechanisms of taught herein are capable of being distributed as a program product in a variety of forms, and that an illustrative embodiment applies equally regardless of the particular type of physical signal bearing media used to actually carry out the distribution. Examples of signal bearing media include, but are not limited to, the following: recordable type media such as floppy disks, hard disk drives, CD ROMs, digital tape, and computer memory.

The various embodiments described above can be combined to provide further embodiments. Aspects of the embodiments can be modified, if necessary, to employ systems, circuits and concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A system to perform in vivo diagnostics on bodily tissue, comprising:
    a transmitter coupled or coupleable to at least one antenna and operable to transmit a plurality of excitation signals at each of a plurality of wavelengths in at least one of a radio frequency band and, or, a microwave frequency band of the electromagnetic spectrum via at least one antenna;
    a receiver coupled or coupleable to at least one antenna and operable to receive a plurality of response signals to the excitation signals which are returned through the bodily tissue via at least one antenna in response to the excitation signals and which represent at least one physical characteristic of the bodily tissue from which the response signals are returned;
    at least one processor; and
    at least one nontransitory processor-readable medium that stores at least one of processor-executable instructions or data which, when executed by the at least one processor, causes the at least one processor to:
    for a first sampling cycle,
        for each of a number of the plurality of wavelengths, determine a sampling difference between a respective excitation signal and a respective response signal at the respective wavelength;
        for each of a number of the plurality of wavelengths, determine a sampling to baseline difference between the determined sampling difference and a respective baseline difference for the respective wavelength, the baseline difference which represents a difference between a baseline excitation signal at the respective wavelength and a baseline response signal at the respective wavelength, each baseline response signal which represent respective response to the respective baseline excitation signal at the respective frequency for a baseline physical condition of the bodily tissue;
        compare at least some of the determined sampling to baseline differences to a defined pattern of differences; and
    indicate an existence or absence of an anomalous physical condition based on the comparison of at least some of the determined sampling to baseline differences to a defined pattern of differences.

2. The system of claim 1, further comprising:
    for a second sampling cycle,
        for each of a number of the plurality of wavelengths, determine a sampling difference between a respective excitation signal and a respective response signal at the respective wavelength;
        for each of a number of the plurality of wavelengths, determine a sampling to baseline difference between the determined sampling difference and a respective baseline difference for the respective wavelength, the baseline difference which represents a difference between a baseline excitation signal at the respective wavelength and a baseline response signal at the respective wavelength, each baseline response signal which represent respective response to the respective baseline excitation signal at the respective frequency for a baseline physical condition of the bodily tissue.

3. The system of claim 2 wherein the at least one of processor-executable instructions or data, when executed by the at least one processor, causes the at least one processor to: compare at least some of the determined sampling to baseline differences to defined pattern of differences for the sampling response signals collected during both the first and the second sampling cycles.

4. The system of claim 2, further comprising:
    for a third sampling cycle,
        for each of a number of the plurality of wavelengths, determine a sampling difference between a respective excitation signal and a respective response signal at the respective wavelength;
        for each of a number of the plurality of wavelengths, determine a sampling to baseline difference between the determined sampling difference and a respective baseline difference for the respective wavelength, the baseline difference which represents a difference between a baseline excitation signal at the respective wavelength and a baseline response signal at the respective wavelength, each baseline response signal which represent respective response to the respective baseline excitation signal at the respective frequency for a baseline physical condition of the bodily tissue.

5. The system of claim 4 wherein the at least one of processor-executable instructions or data, when executed by the at least one processor, causes the at least one processor to: compare at least some of the determined sampling to baseline differences to defined pattern of differences for the sampling response signals collected during the first, the second, and the third sampling cycles.

6. The system of claim 1 wherein the at least one of processor-executable instructions or data, when executed by the at least one processor, causes the at least one processor to:
    for each of the frequencies, average two or more response signals to the respective excitation signal at the respective frequency which are returned through the bodily tissue over a period of time.

7. The system of claim 1 wherein the at least one of processor-executable instructions or data, when executed by the at least one processor, causes the at least one processor to:
    for each of the frequencies, sequentially transmit two or more excitation signals at the respective frequency over a period of time.

8. The system of claim 1 wherein the at least one of processor-executable instructions or data, when executed by the at least one processor, causes the at least one processor to:
ignore at least one response signal to the respective excitation signal for at least one of the frequencies.

9. The system of claim 1 wherein the transmitter transmits the plurality of excitation signals at each of the plurality of discrete frequencies in equal steps or unequal steps from a first frequency to a second frequency.

10. The system of claim 1 wherein the transmitter transmits the plurality of excitation signals at each of the plurality of discrete frequencies in equal steps of 1 MHz from a first frequency to a second frequency.

11. The system of claim 1 wherein the transmitter transmits the plurality of excitation signals at each of the plurality of discrete frequencies in equal steps or unequal steps from a first frequency of approximately 300 MHz to a second frequency.

12. The system of claim 1 wherein the transmitter transmits the plurality of excitation signals at each of the plurality of discrete frequencies in equal steps or unequal steps from a first frequency to a second frequency of approximately 2500 MHz.

13. The system of claim 1 wherein the transmitter transmits the plurality of excitation signals at each of the plurality of discrete frequencies in equal steps or unequal steps from 300 MHz to 2500 MHz.

14. The system of claim 1 wherein the transmitter transmits the plurality of excitation signals at each of the plurality of discrete frequencies in a set of frequencies in equal steps or unequal steps for each of one or more subsets of frequencies in the set of frequencies, and skips one or more frequencies between the subsets of frequencies.

15. The system of claim 1 wherein the transmitter transmits the plurality of excitation signals at each of the plurality of discrete frequencies in a set of frequencies, and skips one or more frequencies associated with one or more natural resonance frequencies of water.

16. The system of claim 1, further comprising:
an interface that interfaces with the bodily tissue, the interface comprising: a first antenna; at least a second antenna, the second antenna spaced laterally offset at any angle with respect to the first antenna by a first range of distances; and at least one electromagnetic force (EMF) shield which electromagnetically isolates the second antenna from the first antenna except via a path that passes through the bodily tissue when the interface is positioned with respect to the bodily tissue.

17. The system of claim 16 wherein the first antenna is communicatively coupleable to the transmitter and the second antenna is communicatively coupleable to the receiver.

18. The system of claim 16 wherein the at least one EMF shield electromagnetically is a sheet of a metal foil.

19. The system of claim 16 wherein the at least one EMF shield electromagnetically isolates the second antenna from a surrounding environment except in a first direction.

20. The system of claim 19 wherein the at least one EMF shield electromagnetically isolates the first antenna from a surrounding environment except in the first direction.

21. The system of claim 20 wherein the first antenna has a main lobe of emission, and the main load of emission of the first antenna extends principally along the first direction.

22. The system of claim 19 wherein the bodily tissue is the epidermis and the first direction faces the epidermis and is spaced therefrom by a second range of distances in use.

23. The system of claim 1 wherein all communications between the transmitter and the receiver are via near field communications without far field communications therebetween.

24. The system of claim 1 wherein the at least one of the processor-executable instructions or data causes the processor to determine whether at least some of the determined sampling to baseline differences are within a range defined by a lower threshold value and an upper threshold value.

25. A method of performing in vivo diagnostics on bodily tissue, comprising:
operating a transmitter coupled or coupleable to at least one antenna to transmit a plurality of excitation signals at each of a plurality of wavelengths in at least one of a radio frequency band and, or, a microwave frequency band of the electromagnetic spectrum via at least one antenna;
receiving via a receiver coupled or coupleable to at least one antenna a plurality of response signals to the excitation signals which are returned through the bodily tissue via at least one antenna in response to the excitation signals and which represent at least one physical characteristic of the bodily tissue from which the response signals are returned;
for a first sampling cycle,
for each of a number of the plurality of wavelengths, determining, via at least one processor, a sampling difference between a respective excitation signal and a respective response signal at the respective wavelength;
for each of a number of the plurality of wavelengths, determining, via at least one processor, a sampling to baseline difference between the determined sampling difference and a respective baseline difference for the respective wavelength, the baseline difference which represents a difference between a baseline excitation signal at the respective wavelength and a baseline response signal at the respective wavelength, each baseline response signal which represent respective response to the respective baseline excitation signal at the respective frequency for a baseline physical condition of the bodily tissue;
comparing, via at least one processor, at least some of the determined sampling to baseline differences to defined pattern of differences; and
causing, via at least one processor, an indicate an existence or absence of an anomalous physical condition to be provided based on the comparison of at least some of the determined sampling to baseline differences to defined pattern of differences.

26. The method of claim 25, further comprising:
for a second sampling cycle,
for each of a number of the plurality of wavelengths, determining, via the at least one processor, a sampling difference between a respective excitation signal and a respective response signal at the respective wavelength; and
for each of a number of the plurality of wavelengths, determining, via the at least one processor, a sampling to baseline difference between the determined sampling difference and a respective baseline difference for the respective wavelength, the baseline difference which represents a difference between a baseline excitation signal at the respective wavelength and a baseline response signal at the respective wavelength, each baseline response signal which represent respective response to the respective baseline excitation signal at the respective frequency for a baseline physical condition of the bodily tissue.

27. The method of claim 26 wherein the comparing at least some of the determined sampling to baseline differences to defined pattern of differences includes comparing at least some of the determined sampling to baseline differences to defined pattern of differences for the sampling response signals collected during both the first and the second sampling cycles.

28. The method of claim 26, further comprising:
for a third sampling cycle,
for each of a number of the plurality of wavelengths, determining, via the least one processor a sampling difference between a respective excitation signal and a respective response signal at the respective wavelength; and
for each of a number of the plurality of wavelengths, determining, via the at least one processor, a sampling to baseline difference between the determined sampling difference and a respective baseline difference for the respective wavelength, the baseline difference which represents a difference between a baseline excitation signal at the respective wavelength and a baseline response signal at the respective wavelength, each baseline response signal which represent respective response to the respective baseline excitation signal at the respective frequency for a baseline physical condition of the bodily tissue.

29. The method of claim 25 wherein comparing at least some of the determined sampling to baseline differences to defined pattern of differences includes comparing at least some of the determined sampling to baseline differences to defined pattern of differences for the sampling response signals collected during the first, the second, and the third sampling cycles.

* * * * *